(12) United States Patent
Krespi et al.

(10) Patent No.: US 10,835,412 B2
(45) Date of Patent: Nov. 17, 2020

(54) SUSPENSION IMPLANT

(71) Applicant: Zelegent, Inc., Irvine, CA (US)

(72) Inventors: Yosef P. Krespi, New York, NY (US); David Volpi, New York, NY (US); Alexander K. Arrow, Lake Forest, CA (US); Joseph F. Paraschac, Campbell, CA (US)

(73) Assignee: ZELEGENT, INC., Irvine, CA (US)

( * ) Notice: Subject to any disclaimer, the term of this patent is extended or adjusted under 35 U.S.C. 154(b) by 120 days.

(21) Appl. No.: 16/145,986

(22) Filed: Sep. 28, 2018

(65) Prior Publication Data

US 2019/0029872 A1  Jan. 31, 2019

Related U.S. Application Data

(63) Continuation of application No. 15/010,640, filed on Jan. 29, 2016, now Pat. No. 10,105,257.

(60) Provisional application No. 62/110,099, filed on Jan. 30, 2015, provisional application No. 62/187,685, filed on Jul. 1, 2015.

(51) Int. Cl.
 *A61F 5/56* (2006.01)
(52) U.S. Cl.
 CPC ............... *A61F 5/566* (2013.01); *A61F 5/56* (2013.01)
(58) Field of Classification Search
 CPC .................................. A61F 5/566; A61F 5/56
 See application file for complete search history.

(56) References Cited

U.S. PATENT DOCUMENTS

| | | | |
|---|---|---|---|
| 4,950,285 | A | 8/1990 | Wilk |
| 5,931,855 | A | 8/1999 | Buncke |
| 6,250,307 | B1 | 6/2001 | Conrad et al. |
| 6,401,717 | B1 | 6/2002 | Conrad et al. |
| 6,513,531 | B2 | 2/2003 | Knudson et al. |
| 8,246,652 | B2 | 8/2012 | Ruff |
| 8,721,681 | B2 | 5/2014 | Leung |
| 2002/0077661 | A1 | 6/2002 | Saadat |

(Continued)

FOREIGN PATENT DOCUMENTS

EP    1858243    11/2009

OTHER PUBLICATIONS

International Search Report and Written Opinion dated Jul. 29, 2016 issued for International PCT Application No. PCT/US2016/15682.

*Primary Examiner* — Christine H Matthews
*Assistant Examiner* — Joshua Daryl D Lannu
(74) *Attorney, Agent, or Firm* — K&L Gates LLP

(57) ABSTRACT

In an embodiment, a surgical implant includes a body extending from a distal end to a proximal end, the body having a first section proximal to the distal end and a second section between the first section and the proximal end, a needle attachment member located at the distal end of the body, the needle attachment member configured to attach to a needle for insertion of the surgical implant into a patient's tissue, a plurality of first barbs located on the first section of the body, the first barbs pointed towards the proximal end of the body, and a plurality of second barbs located on the second section of the body, the second barbs pointed towards the distal end of the body, wherein the second barbs are configured to be folded inwardly for insertion of the surgical implant into the patient's tissue by the needle.

20 Claims, 17 Drawing Sheets

(56) References Cited

U.S. PATENT DOCUMENTS

2003/0236570 A1\* 12/2003 Cook .................. A61F 2/848
 623/1.36
2009/0210006 A1 8/2009 Cohen
2010/0108077 A1\* 5/2010 Lindh .................. A61F 5/566
 128/848

\* cited by examiner

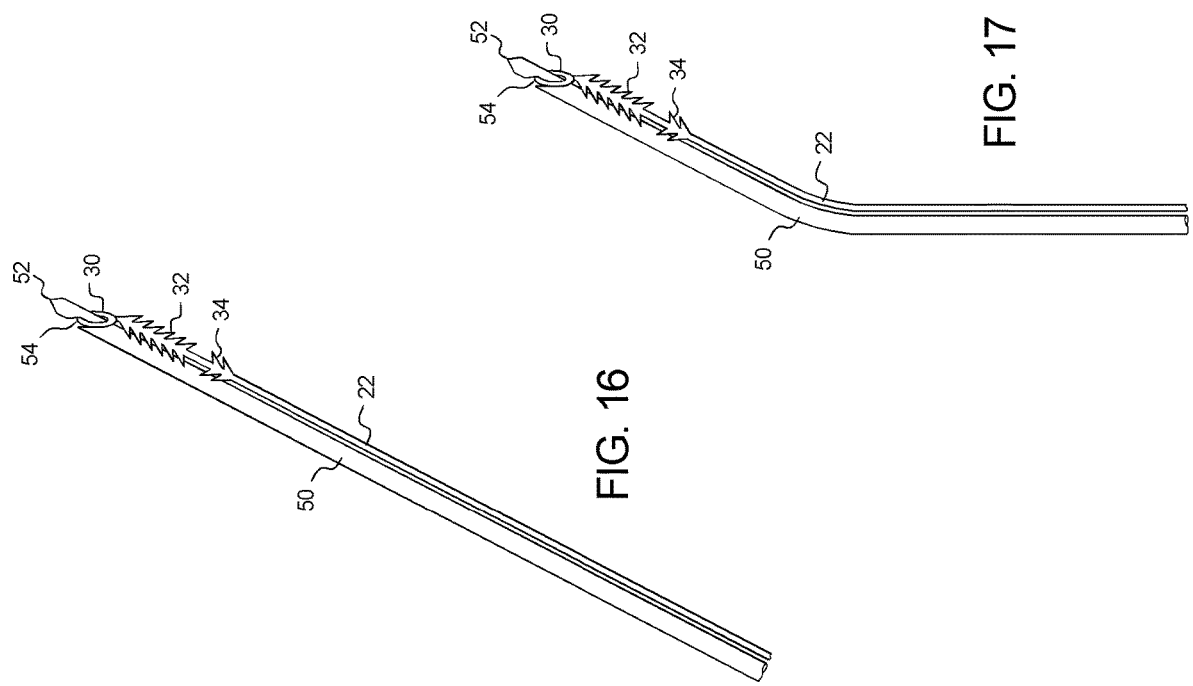

SUSPENSION IMPLANT

PRIORITY CLAIM

This application is a continuation of U.S. application Ser. No. 15/010,640, entitled, "Suspension Implant", filed Jan. 29, 2017, which claims priority to U.S. Provisional Patent Application No. 62/110,099, entitled "Suspension Implant", filed Jan. 30, 2015, and to U.S. Provisional Patent Application No. 62/187,685, entitled "Suspension Implant", filed Jul. 1, 2015, the entire contents of each of which are hereby incorporated by reference and relied upon.

FIELD OF THE INVENTION

The present disclosure relates generally to methods and apparatuses for lifting, suspending and/or stiffening a patient's tissue, and more specifically to suspension implants designed to lift, suspend and stiffen a patient's soft palate and/or uvula.

CROSS REFERENCE TO APPLICATIONS

This application expressly incorporates by reference, and makes a part hereof, U.S. patent application Ser. No. 14/494,278, filed Sep. 23, 2014, entitled "Surgical Procedure and Related Apparatus for Treating Sleep Apnea by Lifting, Suspending and Stiffening the Soft Palate".

BACKGROUND

Approximately 20% of the adult population of the developed world consistently snores at night at volumes high enough to disturb sleeping partners. This results in strained relationships and the possible breakdown of the family unit, as well as real physiologic harm to the snorer. Of audible snorers, approximately one in five suffers from obstructive sleep apnea (OSA), a condition in which tissues of the nasopharynx fall into positions that block the airway, restricting breathing during sleep to an extent that causes the patient repeated cycles of breathing cessation (apnea) and subsequent gasping for air without regaining consciousness. The OSA patient is deprived of restful sleep and suffers from poor tissue oxygenation, impaired memory, cognition, and daytime mental functioning, and in extreme cases runs the risk of sudden death from oxygen deprivation (asphyxiation) during sleep.

Remedies for OSA start with prescribed weight loss, as approximately 25% of OSA patients can be cured by losing significant fat around the neck. The majority of OSA patients, however, are not obese. For them, the "gold standard" therapy is continuous positive airway pressure (CPAP) treatment. This non-surgical approach to treating OSA involves requiring the patient to wear a head-mounted electric-powered breathing apparatus every night, which mechanically forces air down the patient's windpipe, blowing open the floppy tissue that would otherwise be obstructing the nasopharynx with each breath cycle. The obvious disadvantage of CPAP therapy is that it is unpleasant at best and psychologically debilitating at worst to a patient's nightlife, not to mention uncomfortable to wear.

Less unpleasant, but similarly requiring patient compliance with nightly rituals, is the use of mandible-displacing dental appliances. These devices are similar to dental "night guards" commonly used to prevent teeth grinding (nocturnal bruxism), such as "Silent Nite" or "Pivot Solution." They have the added feature of a configuration that pushes the mandible forward (in the ventral direction in the sagittal plane) to cause the base of the tongue to move away from the back of the throat, thereby opening the airway. An implantable electronic Tongue Nerve Stimulator (the Inspire II Upper Airway Stimulation System) has also been FDA cleared and is being used in severe OSA cases in which the treating physician is confident that the patient's obstruction is specifically due to the tongue and not the palate tissues. These devices suffer from a significant limitation, however, because only approximately 10% of non-obese snorers owe their condition to tongue-base airway obstruction. In the vast majority of snoring and mild OSA cases, the soft palate and uvula are the cause of the obstruction. These tissues become longer and floppier with age, making OSA increasingly common in advancing decades.

Two approaches have been commercialized to directly intervene and correct the soft palate's tendency to fall back and block the airway. In 1990, Dr. Yves-Victor Kamami, a surgeon of the Marie-Louise Clinic in France published reports of his short-term success treating OSA with a surgical procedure he called Laser-assisted Uvulopalatoplasty (LAUP). This procedure enjoyed popularity in over the next ten years, until the late 1990s when additional publications (Finkelstein, Schmidt and others) showed that in many cases, laser-assisted uvulopalatoplasty for moderate snorers without OSA ("nonapneic snorers") could cause OSA to begin, or worsen existing mild OSA, attributable to thermal damage inflicted by the laser. The laser appeared to cause scar tissue that crowded and thereby reduced the airspace in the pharynx (it induced progressive palatal fibrosis, accompanied by medial traction of the posterior tonsillar pillars leading to velopharyngeal insufficiency). Scar tissue also tends to make the airway more likely to collapse during sleep, since it lacks the resiliency of healthy tissue. Hence, LAUP could be a medically-induced ("iatrogenic") cause of sleep apnea.

In 2003, Restore Medical launched the Pillar Palatal Implant System, consisting of a hollow-bore needle handheld applicator that deployed a stiff rod-shaped implant into a patient's soft palate. A physician would deploy an average of 2-3 Pillar rods as permanent implants to stiffen the palate and thereby make it less likely to obstruct the airway. The main challenges were that (1) the Pillar implants, no matter how many are used, do not shorten the soft palate, and therefore cannot pull it away from the sit of obstruction, and (2) the implants had a persistent rate of partial extrusion in the post-procedure period.

SUMMARY

The present disclosure is directed to methods and apparatuses that may be employed to lift, suspend and/or stiffen a patient's tissue. In a general example embodiment, a surgical implant includes a body having a distal end and a proximal end, a needle attachment member located at the distal end of the body, a plurality of first barbs located on the body proximal to the distal end, the plurality of first barbs pointed towards the proximal end of the body, and a plurality of second barbs located on the body between the plurality of first barbs and the proximal end, the plurality of second barbs pointed towards the distal end of the body.

In another general example embodiment, a surgical implant includes a body having a distal end, a proximal end and a functional length located proximal to the distal end, the functional length including a first length and a second length, a plurality of first barbs located within the first length proximal to the distal end, the plurality of first barbs pointed towards the proximal end of the body, and a plurality of second barbs located within the second length between the plurality of first barbs and the proximal end, the plurality of second barbs pointed towards the distal end of the body, wherein the first length only includes barbs pointed towards the proximal end of the body and the second length only includes barbs pointed towards the distal end of the body.

In another general example embodiment, a surgical implant includes a body having a distal end and a proximal end, a needle attachment member located at the distal end of the body, and a plurality of barbs located on the length of the body proximal to the needle attachment member, wherein the length of the body proximal to the needle attachment member only includes barbs pointed towards the proximal end of the body.

In another general example embodiment, a method of lifting and stiffening a patient's tissue includes attaching a needle attachment member of a suspension implant to a tip of a needle, the needle attachment member located at a distal end of the suspension implant, inserting at least the tip of the needle into the patient's tissue in a first direction while the patient's tissue is in an initial position, removing the needle from the patient's tissue, pulling the suspension implant in a second direction so that a plurality of first barbs of the suspension implant pointed towards a proximal end of the suspension implant pull the patient's tissue in the second direction, and releasing the suspension implant so that a plurality of second barbs of the suspension implant pointed towards the distal end of the suspension implant prevent the patient's tissue from returning to the initial position.

In another general example embodiment, a kit for lifting and stiffening a patient's tissue includes a container including a first implant including a first body having a first distal end and a first proximal end, a first needle attachment member located at the first distal end, a first plurality of first barbs located on the first body proximal to the first distal end and pointed towards the first proximal end, and a first plurality of second barbs located on the first body between the first plurality of first barbs and the first proximal end and pointed towards the first distal end, and a second implant including a second body having a second distal end and a second proximal end, a second needle attachment member located at the second distal end, a second plurality of first barbs located on the second body proximal to the second distal end and pointed towards the second proximal end, and a second plurality of second barbs located on the second body between the second plurality of first barbs and the second proximal end and pointed towards the second distal end, wherein the first implant and the second implant differ in at least one of: (i) the size of the first plurality of first barbs and the first plurality of second barbs; (ii) the size of the second plurality of first barbs and the second plurality of second barbs; (iii) the length along the first body of the first plurality of first barbs and the length along the second body of the second plurality of first barbs; (iv) the length along the first body of the first plurality of second barbs and the length along the second body of the second plurality of second barbs; (v) the presence or absence of a distal anchor; (vi) the presence or absence of a proximal anchor; (vii) the presence or absence of a treble hook anchor; (viii) the curvature of the first plurality of first barbs and the first plurality of second barbs; and (ix) the curvature of the second plurality of first barbs and the second plurality of second barbs.

In another general example embodiment, a surgical implant includes a body having a distal end and a proximal end, the distal end including a needle attachment member configured to be inserted into a patient's soft tissue in a first direction, means for pulling the patient's tissue in a second direction with a plurality of first barbs pointed towards the proximal end, and means for preventing the patient's tissue from returning to an initial position using a plurality of second barbs pointed towards the distal end.

In another general example embodiment, a surgical implant includes an elongated body having a distal end and a proximal end, a needle attachment member located at the distal end of the body, a proximal loop located at the proximal end of the body, a plurality of first barbs located on the body proximal to the distal end, the plurality of first barbs pointed towards the proximal end of the body, and a plurality of second barbs located on the body proximal to the proximal end, the plurality of second barbs pointed towards the distal end of the body.

In another general example embodiment, a surgical implant includes an elongated body having a distal end and a proximal end, a needle attachment member located at the distal end of the body, a proximal loop located at the proximal end of the body, and a plurality of barbs located on the body between the distal loop and the proximal loop.

In another general example embodiment, a device for inserting a surgical implant into a patient's soft tissue includes a curved body including an insertion tip configured to pierce the patient's soft tissue, the curved body having a convex side and an opposing concave side, an elongated indentation located on the convex side of the curved body, and an implant receiving member located between the insertion tip and the elongated indentation on the convex side of the curved body.

In another general example embodiment, a system for lifting and stiffening a patient's tissue includes a surgical implant including an elongated body with a plurality of barbs and a distal end including a needle attachment member, and a device for inserting the surgical implant into the patient's tissue, the device including a curved body having a sharp tip, a receiving member located proximal to the sharp tip and configured to receive the needle attachment member of the surgical implant, and an indentation configured to receive the plurality of barbs.

In another general example embodiment, a method of lifting and stiffening a patient's tissue includes attaching a needle attachment member of a suspension implant to a tip of a needle, the needle attachment member located at a distal end of the suspension implant, securing a proximal loop of the suspension implant, the proximal loop located at a proximal end of the suspension implant, inserting at least the tip of the needle into the patient's tissue in a first direction while the patient's tissue is in an initial position, removing the needle from the patient's tissue, pulling the suspension implant in a second direction so that a plurality of first barbs of the suspension implant pointed towards the proximal end of the suspension implant pull the patient's tissue in the second direction, and releasing the proximal loop of the suspension implant so that a plurality of second barbs of the suspension implant pointed towards the distal end of the suspension implant prevent the patient's tissue from returning to the initial position.

In another general example embodiment, a surgical implant includes a body having a distal end and a proximal end, a needle attachment member located at the distal end of the body, one or more first barbs located on the body proximal to the distal end, the one or more first barbs pointed towards the proximal end of the body, and one or more second barbs located on the body between the one or more first barbs and the proximal end, the one or more second barbs pointed towards the distal end of the body.

In another general example embodiment, a surgical implant includes an elongated body having a distal end and a proximal end, a needle attachment member located at the distal end of the body, a proximal loop located at the proximal end of the body, one or more first barbs located on the body proximal to the distal end, the one or more first barbs pointed towards the proximal end of the body, and one or more second barbs located on the body proximal to the proximal end, the one or more second barbs pointed towards the distal end of the body.

BRIEF DESCRIPTION OF THE FIGURES

Embodiments of the present disclosure will now be explained in further detail by way of example only with reference to the accompanying figures, in which:

FIG. 16 shows an example embodiment of a suspension implant according to the present disclosure being attached to an example embodiment of a needle according to the present disclosure;

FIG. 17 shows an example embodiment of a suspension implant according to the present disclosure being attached to an example embodiment of a needle according to the present disclosure;

DETAILED DESCRIPTION

No snoring-correction technology yet exists that shortens and stiffens the soft palate. There is therefore a pressing need for a device that will allow physicians to shorten and stiffen snoring and mild OSA patients' soft palates in a simple office-based procedure.

Before the disclosure is described, it is to be understood that this disclosure is not limited to the particular apparatuses and methods described. It is also to be understood that the terminology used herein is for the purpose of describing particular embodiments only, and is not intended to be limiting, since the scope of the present disclosure will be limited only to the appended claims.

As used in this disclosure and the appended claims, the singular forms "a," "an" and "the" include plural referents unless the context clearly dictates otherwise. The methods and apparatuses disclosed herein may lack any element that is not specifically disclosed herein. Thus, "comprising," as used herein, includes "consisting essentially of" and "consisting of."

Figure 1:
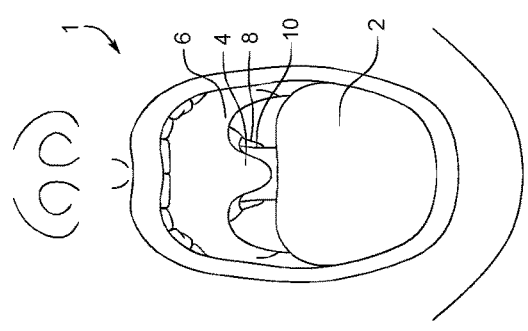
FIG. 1 shows a front view of an example mouth of a snoring patient.
Figure 2:
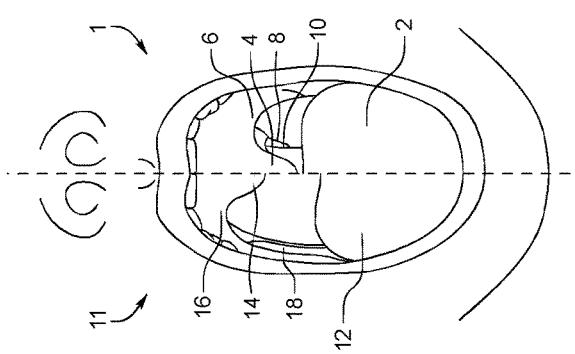
FIG. 2 shows a front view comparing an example mouth of a non-snoring patient to the mouth of FIG. 1.

FIG. 1 illustrates an example mouth 1 of a typical snoring patient. FIG. 2 compares the mouth 1 of the snoring patient in FIG. 1 to an example mouth 11 of a non-snoring patient. The snoring patient's mouth 1 has a higher tongue base 2, an enlarged uvula 4, a long, low, thick palate 6, a large tonsil 8 and a vertical pharyngeal fold 10. In comparison, the non-snoring patient's mouth 11 has a lower tongue base 12, a smaller, higher uvula 14, a high, thin palate 16, a small tonsil 18 and no vertical pharyngeal fold. These differences between the snorer's mouth 1 and the non-snorer's mouth 11 can cause the snorer's upper airway to become obstructed.

The present disclosure seeks to correct at least the large uvula 4 and/or the thick palate 6 of the snoring patient's mouth 1 by providing a suspension implant and a method of using a suspension implant as described herein. As described in more detail below, the method according to the present disclosure works by deploying two or three resorbable barb-tipped suspension implants into the soft palate and/or uvula, each suspension implant having an end shaped like a miniature harpoon and a needle attachment member, such as a distal loop, to be pushed into the tissue by a crochet-hook-like tool. The harpoon-like implants are inserted into the palate, then pulled back with proximal reverse-direction barbs to prevent slippage. This shortens and stiffens the soft palate in a direct, elegant and effective way to stop the soft palate tissues and uvula from touching the back of the nasopharynx. Patients are left with an open airway that allows for uninterrupted sleep, without having to think about any recurring procedure, and free from worry about an implant extrusion.

Figure 3:
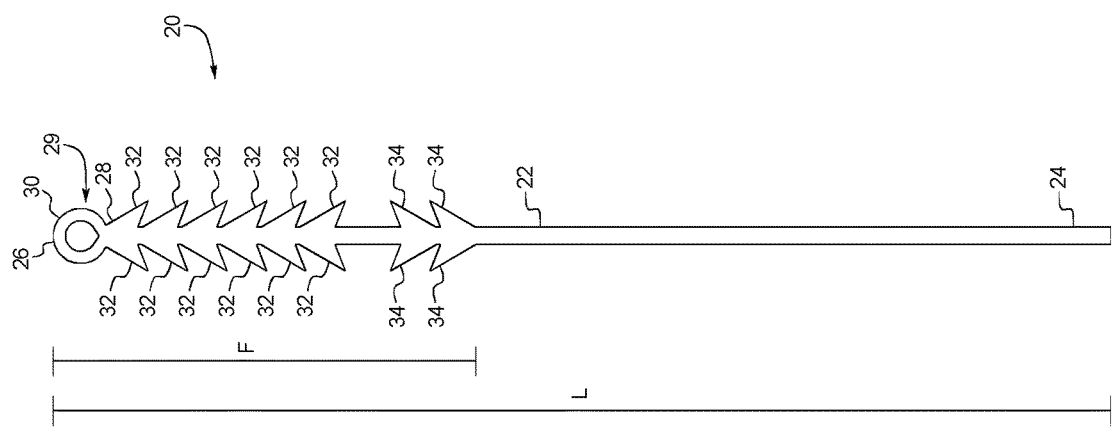
FIG. 3 shows an example embodiment of a suspension implant according to the present disclosure.

FIG. 3 illustrates an example embodiment of a palatal suspension implant 20 according to the present disclosure. In the illustrated embodiment, suspension implant 20 includes an elongated body 22 having a proximal end 24 and a distal end 26, a pointed tip 28 and a needle attachment member 29 located at the distal end 26, a plurality of first barbs 32, and a plurality of second barbs 34. In the illustrated embodiment, the needle attachment member 29 includes a distal loop 30. In use, suspension implant 20 can be inserted into a patient's soft-palate in a first direction, leading with the distal end 26 of body 22. The proximal end 24 body 22 can then be pulled in a second direction, preferably opposite the first direction, to shorten and stiffen the patient's soft palate. As proximal end 24 is pulled in the second direction, the plurality of first barbs 32, which are pointed towards the proximal end 24 of suspension implant 20, grab hold of the patient's soft palate for the lifting and raising.

In an embodiment, the functional length F of suspension implant 20 can be approximately 2.0 to 3.5 centimeters, and the total length L of suspension implant 20 can be approximately 30 centimeters. The functional length F of suspension implant 20 is the length of the portion of body 22 that is inserted into the patient's soft palate and/or uvula. For example, if the functional length F of suspension implant 20 is 2.0 centimeters, then the body 22 of suspension implant 20 is inserted approximately 2.0 centimeters deep into the patient's soft palate and/or uvula. In another embodiment, the length L can be between 1 and 30 centimeters, the thickness of the body can be between about 0.5 millimeters and 3 millimeters.

In an embodiment, the suspension implant 20 is a flexible, dissolvable material such as a polyester material, for example, a biodegradable thermoplastic aliphatic polyester material such as polyglactic acid, polycaprolactone, polylactic Acid (PLA), or polyglycolic Acid (PGA). Preferably, the material dissolves in a time period sufficient to allow the patient's soft palate and/or uvula to permanently suspend and stiffen, for example, three months. In alternative embodiments, suspension implant 20 can be made of a non-dissolvable material or a material that dissolves in more or less than three months. In another embodiment, suspension implant 20 can include a polycarbonate polyurethane material around body 22 to increase strength.

Figure 4:
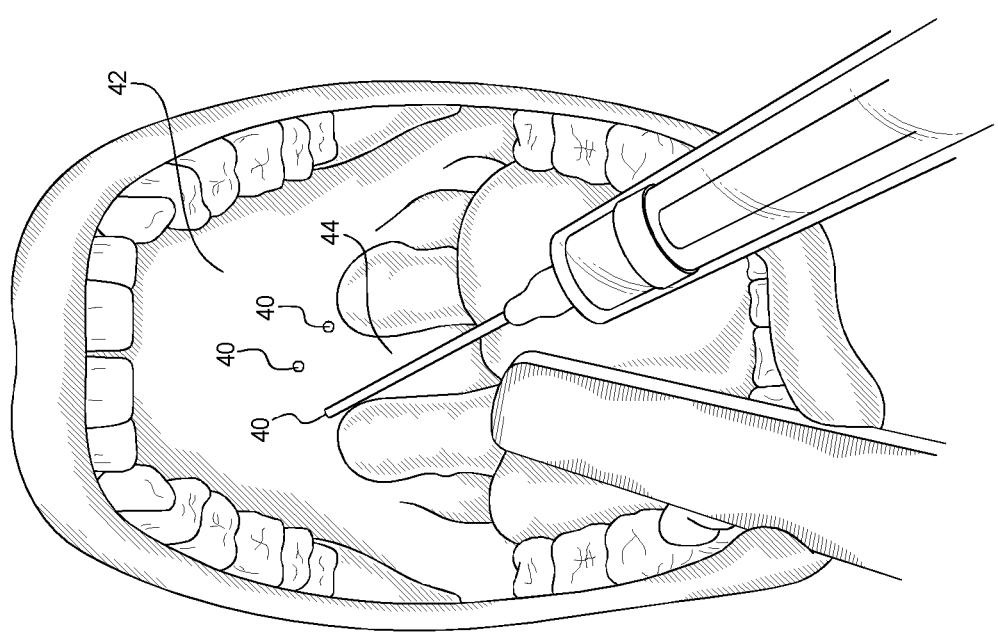
FIG. 4 shows a front view of an example mouth of a snoring patient.

In an embodiment, the disclosed method begins by applying a local anesthesia to a patient's soft palate. Preferably, two cubic centimeters of 2% lidocaine with 1:100,000 epinephrine is injected at three different points 40 in the patient's soft palate 42, above the uvula 44 and near the location where one or more suspension implants 20 will be inserted into the soft palate, as shown in FIG. 4. The injection should be slow and intramuscular and can take effect within minutes.

Once the patient has been anesthetized, one or more suspension implants 20 can be inserted into the patient's soft palate 42 by leading with distal end 26. The suspension implants 20 can be inserted using a needle 50, which can be a plain needle or the needle end of a suture insertion device, such as the suture insertion devices described in U.S. patent application Ser. No. 14/494,278, which is incorporated by reference herein in its entirety. In an embodiment, the needle 50 includes crochet-hook-type insertion tip where the needle 50 pierces the patient's soft palate 42. In an embodiment, two or three suspension implants 20 are inserted about 25 to 30 millimeters through the patient's soft palate, to an area approximately 8 to 10 millimeters from the distal ridge of the soft palate. In an embodiment, one suspension implant 20 is inserted along the patient's midline and advanced straight back distally, and the other two suspension implants 20 are inserted approximately 5 to 10 millimeters laterally on each side, and advanced back in a slight radiating pattern, so that the tips end up approximately 10 to 15 millimeters lateral to the distal end of the fully-advanced middle suture implant. In another embodiment, two suspension implants 20 are placed approximately 5 to 10 millimeters lateral to the patient's midline and advanced back distally, in a slight radiating pattern, so that the tips end up approximately 16 to 20 millimeters apart from each other, each 8 to 10 millimeters lateral to the midline of the uvula.

To insert a suspension implant 20 into the patient's soft palate 42, the needle attachment member 29 of the suspension implant 20 is first attached to the insertion tip 52 of the needle 50. The needle attachment member 29 is important in this respect because it allows the suspension implant 20 to be inserted into the patient's soft palate 42 without the suspension implant 20 having to be folded over or through a tip of a needle. In other words, needle attachment member 29 allows suspension implant 20 to be inserted straight into the patient's soft palate at distal end 26 without any twisting or folding or knotting of suspension implant 20. That is, needle attachment member 29 allows the needle 50 to drive suspension implant 20 into the tissue.

In the illustrated embodiment, needle attachment member 29 includes a distal loop 30 that can be attached to a crochet-like needle tip 52 at an aperture 54 proximal to tip 52, as shown in FIGS. 16 and 17. As illustrated in FIG. 17, a curved needle 50 can advantageously be used for easier insertion into the patient's soft palate. It should be understood that the distal loop 30 can be open, as shown in the drawings with an aperture all the way therethrough, or can be closed, for example by a cup-shaped loop that can grip a protuberance but does not have an aperture entirely therethough. Needle attachment member 29 can similarly include a protuberance on the suspension implant 20 that can attach to a slot or corresponding protuberance on the needle. Although a distal loop is shown in the drawings herein, it should be understood that the distal loops disclosed herein can be replaced by other needle attachment members 29 that allow the suspension implant 20 to be easily attached to the needle and detached once the needle has been inserted into the patient's tissue.

Figure 18:
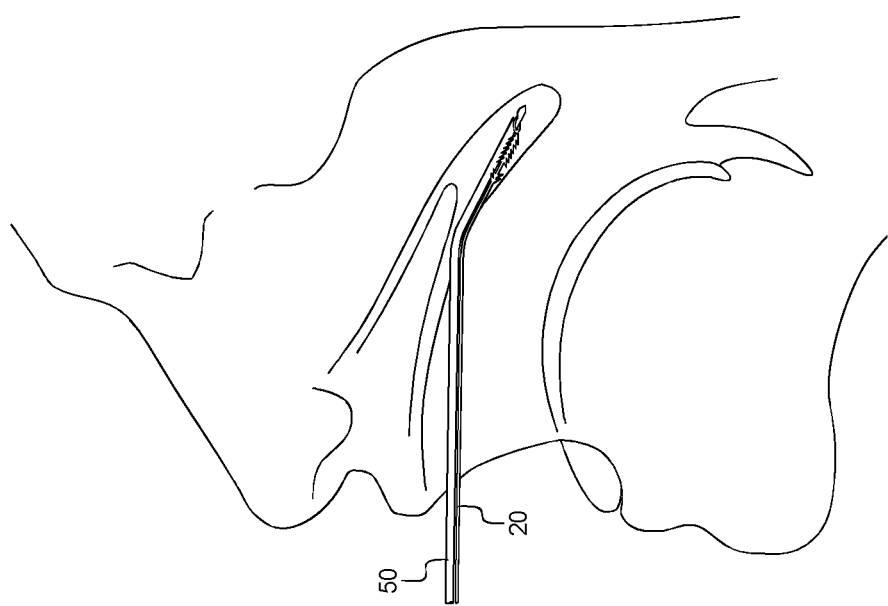
FIG. 18 shows the needle embodiment of FIG. 16 being inserted into a patient's soft palate.

Once attached to the insertion tip 52 of needle 50, suspension implant 20 can be inserted into the patient's soft palate 42 by inserting the needle 50 in a first direction into the patient's soft palate 42 so that the insertion tip 52 of the needle 50 extends into the soft palate 42 and optionally also into the base of the uvula 44. Needle 50 can be inserted into the soft palate 42 so that the tip of the needle 50 extends to the base of the uvula 24. Preferably, needle 50 is inserted deep enough into the patient's soft palate 42 and/or uvula 44 so that the entire functional length F of suspension implant 20 is located within the patient's soft palate 42 and/or uvula 44. Sharp tip 28 of suspension implant 20 assists in the insertion of suspension implant 20 into the patient's soft palate 42. FIG. 18 (not to scale) shows needle 50, with suspension implant 20 attached, as needle 50 is being inserted into the patient's soft palate 42.

Once the needle 50 and suspension implant 20 have been inserted into the patient's soft palate 42 and/or uvula 44, the needle 50 can be removed from the patient's soft palate 42 and/or uvula 44 in a direction opposite of the insertion direction. When the needle 50 is being removed, the insertion tip 52 of the needle 50 is released from the needle attachment member 29 (distal loop 30) of the suspension implant 20 so that the functional length of the suspension implant 20 remains in the patient's soft palate 42 and/or uvula 44 and only the needle 50 is removed from the patient.

Once the needle 50 has been removed from the patient's tissue, the proximal end 24 of suspension implant 20 can be pulled in a second direction to shorten and stiffen the patient's soft palate 42 and/or uvula 44. In an embodiment, the second direction is substantially opposite to the first insertion direction of the needle 50 and the suspension implant 20 into the patient's soft palate. In alternative embodiments, the second direction can be angled with respect to the first insertion direction so as to pull the tissue in a different direction desired by a doctor. Since many patients have differently shaped palates and uvulas, the first and second directions can change from patient to patient.

The plurality of first barbs 32 of the suspension implant 20 are located proximal to the needle attachment member 29, here distal loop 30. As the proximal end 24 of the suspension implant 20 is pulled in the second direction, the pointed tips of each of the plurality of first barbs 32 grab and pull the patient's tissue located near the distal end 26 of body 22, namely, the portion of the patient's soft palate 42 and/or uvula 44 that is obstructing the patient's breathing. The plurality of first barbs 32 are pointed towards the proximal end 24 of suspension implant 20, so the pointed tips of the plurality of first barbs 32 are positioned to dig into the patient's tissue and pull the patient's tissue in the second direction as the plurality of first barbs 32 move in the second direction. This pulling results in the uvula 42 being raised, and the patient's tissue being compressed. In an embodiment, suspension implant 20 includes between 1 and 20 first barbs.

Once the patient's soft palate 42 and/or uvula 44 has been raised by the plurality of first barbs 32, the body 22 of suspension implant 20 can be cut between the proximal end 24 and the plurality of second barbs 34. Preferably, suspension implant 20 is cut while the suspension implant is in tension from being pulled in the second direction, and the cut should be at the portion of body 22 that is close to the original insertion point of the needle 50 into the patient's soft palate 42. The purpose of cutting suspension implant 20 is so that no portion of suspension implant 20 is hanging from the patient's mouth when the procedure is finished.

After the body 22 of suspension implant 20 is cut, the functional length F of the suspension implant 20 still in the patient's soft palate will slightly pull back in the first direction due to the release of the tension in body 22 from being pulled in the second direction. The plurality of second barbs 34, however, will prevent the patient's soft palate 42 and/or uvula 44 from falling back to its initial position because the plurality of second barbs 34 are pointed towards the distal end 26 of suspension implant 20, so the tips of the plurality of second barbs 34 are positioned to dig into the patient's tissue and resist the initial, first direction. With the plurality of first barbs 32 raising the patient's soft tissue 42 and/or uvula 44 and resisting movement of the patient's soft tissue 42 and/or uvula 44 in the second direction, and the plurality of second barbs 34 resisting movement of the patient's soft tissue 42 and/or uvula 44 in the first direction, the patient's tissue is compressed and remains in a raised position. One advantage of suspension implant 20 is that there is no need to tie any knots in suspension implant 20 to lift and suspend the patient's tissue because the lifting and suspending is performed entirely by the positioning of the plurality of first barbs 32 and the plurality of second barbs 34.

In the illustrated embodiment, suspension implant 20 includes more first barbs 32 than second barbs 34, and the length along body 22 of the plurality of first barbs 32 is longer than the length along body 22 of the plurality of second barbs 34. This configuration is easier to insert into the patient's soft palate 42 and/or uvula 34 because the pointed direction of the first barbs 32 allows the longer length of the plurality of first barbs 32 along body 22 to easily slide into the patient's soft palate, whereas the shorter length of the plurality of second barbs 34 along body 22 will resist the insertion direction due to the second barbs being pointed towards distal end 26 and against the insertion direction. Thus, in an embodiment, the functional length F of body 22 will include a first length located near the distal end and having only a plurality of first barbs 32 that point towards the proximal end 24, and a second length located at the proximal portion of functional length F and having only a plurality of second barbs 34 that point towards the distal end 26.

FIGS. 5 to 14 show alternative example embodiments of suspension implants according to the present disclosure. It should be understood that any of the features of suspension implant 20 can be used on any of the suspension implant embodiments illustrated in FIGS. 5 to 14, and vice versa.

Figure 5:
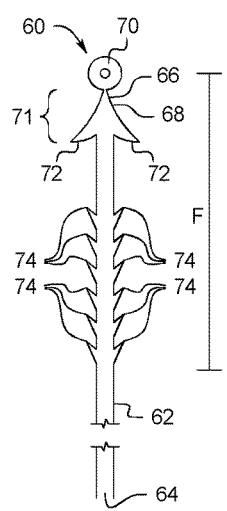
FIG. 5 shows an example embodiment of a suspension implant according to the present disclosure.

FIG. 5 is an alternative example embodiment of a suspension implant 60 according to the present disclosure. In the illustrated embodiment, suspension implant 60 includes an elongated body 62 having a proximal end 64 and a distal end 66, a pointed tip 68 and a needle attachment member such as a distal loop 70 located at the distal end 64, a distal anchor 71 having a plurality of first barbs 72, and a plurality of second barbs 74. As illustrated, the plurality of first barbs 72 on distal anchor 71 are larger than the plurality of second barbs 72. That is, the first barbs 72 form a large anchor 71 at the distal end 66 of the suspension implant 60 to provide a larger lifting force and suspend the patient's soft palate 42 and/or uvula 44 as the suspension implant 60 is pulled in the second direction after insertion. The smaller second barbs 74 can dig into the patient's tissue and resist movement in the patient's tissue in the first insertion direction, thereby working in conjunction with the first barbs 72 to compress the patient's tissue and hold the patient's tissue in a raised position.

Figure 6:
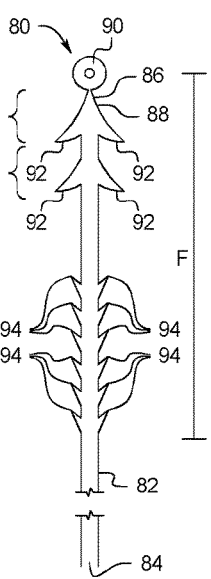
FIG. 6 shows an example embodiment of a suspension implant according to the present disclosure.

FIG. 6 is an alternative example embodiment of a suspension implant 80 according to the present disclosure. In the illustrated embodiment, suspension implant 80 includes an elongated body 82 having a proximal end 84 and a distal end 86, a pointed tip 88 and a needle attachment member such as a distal loop 90 located at the distal end 86, two distal anchors 91 having a plurality of first barbs 92, and a plurality of second barbs 94. Suspension implant 80 is similar to suspension implant 60 but the plurality of first barbs 92 are located at two distal anchors 91 near the distal end 86, as compared to one distal anchor for suspension implant 60. The extra anchor 91 provides added pull at the distal end 86 of suspension implant 80, which can be used to accommodate patients with relatively muscular tissue in the soft palate 42 and/or uvula 44.

Figure 7:
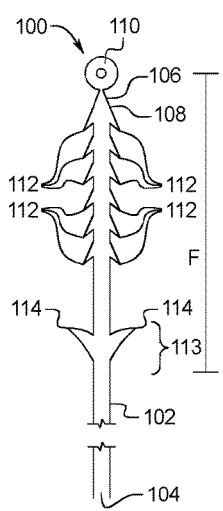
FIG. 7 shows an example embodiment of a suspension implant according to the present disclosure.

FIG. 7 is an alternative example embodiment of a suspension implant 100 according to the present disclosure. In the illustrated embodiment, suspension implant 100 includes an elongated body 102 having a proximal end 104 and a distal end 106, a pointed tip 108 and a needle attachment member such as a distal loop 110 located at the distal end 106, a plurality of first barbs 112, and a proximal anchor 113 having a plurality of second barbs 114. As illustrated, the plurality of second barbs 114 on proximal anchor 113 are larger than the plurality of first barbs 112. That is, the second barbs 114 form a large anchor near the proximal side of the functional length F of suspension implant 100 to resist movement of the suspension implant 100 in the first insertion direction, thereby working in conjunction with the first barbs 112 to compress the patient's tissue and hold the patient's tissue in a raised position. Locating the larger proximal anchor 113 near the proximal side of the functional length F of suspension implant 100 helps to accommodate patients with relatively muscular tissue to prevent the tissue from dropping after the tension in suspension implant 100 is released during implantation, as described above.

Figure 8:
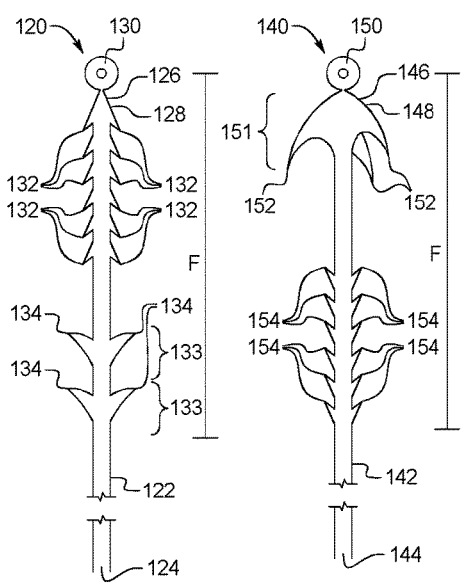
FIG. 8 shows an example embodiment of a suspension implant according to the present disclosure.

FIG. 8 is an alternative example embodiment of a suspension implant 120 according to the present disclosure. In the illustrated embodiment, suspension implant 120 includes an elongated body 122 having a proximal end 124 and a distal end 126, a pointed tip 128 and a needle attachment member such as a distal loop 130 located at the distal end 126, a plurality of first barbs 132, and two proximal anchors 133 having a plurality of second barbs 134. Suspension implant 120 is similar to suspension implant 100 but the plurality of second barbs 134 are located at two proximal anchors 133 near the proximal side of the functional length F of suspension implant 120, as compared to one proximal anchor for suspension implant 100. The extra anchor 133 provides added resistance at the proximal side of the functional length F of the suspension implant 120, which can be used to accommodate patients with relatively muscular tissue in the soft palate 42 and/or uvula 44.

Figure 9:
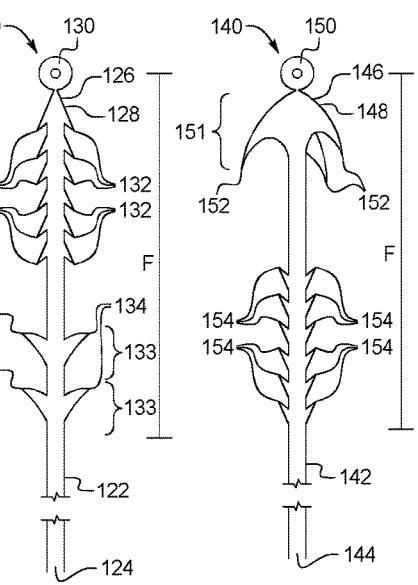
FIG. 9 shows an example embodiment of a suspension implant according to the present disclosure.

FIG. 9 is an alternative example embodiment of a suspension implant 140 according to the present disclosure. In the illustrated embodiment, suspension implant 140 includes an elongated body 142 having a proximal end 144 and a distal end 146, a pointed tip 148 and a needle attachment member such as a distal loop 150 located at the distal end 146, a harpoon-like treble hook anchor 151 having a plurality of first barbs 152, and a plurality of second barbs 154. Suspension implant 140 is similar to suspension implant 60 but the plurality of first barbs 152 are located at a harpoon-like treble hook anchor 151 near the distal end 146. Treble hook anchor 151 is relatively larger than distal anchor 71 of suspension implant 60, has more first barbs 152, and the curvature of the barbs 152 is more towards the proximal end of suspension implant 140 as opposed to being curved more radially outward as with suspension implant 60. Harpoon-like treble hook anchor 151 provides added resistance at the distal end 146 of suspension implant 140, which can be used to accommodate patients with relatively muscular tissue in the soft palate 42 and/or uvula 44.

Figure 10:
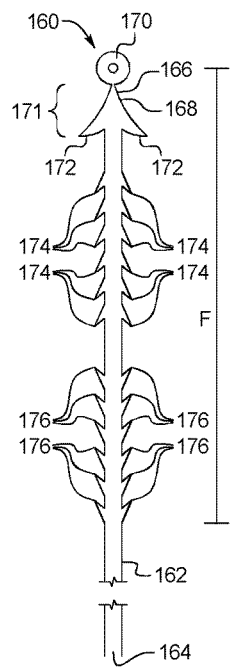
FIG. 10 shows an example embodiment of a suspension implant according to the present disclosure.

FIG. 10 is an alternative example embodiment of a suspension implant 160 according to the present disclosure. In the illustrated embodiment, suspension implant 160 includes an elongated body 162 having a proximal end 164 and a distal end 166, a pointed tip 168 and a needle attachment member such as a distal loop 170 located at the distal end 166, a plurality of first barbs 172, 174, and a plurality of second barbs 174. Suspension implant 160 is similar to suspension implant 60 but includes two different sizes of first barbs 172, 174. First barbs 172 are located at distal anchor 171, are closer to distal end 166, and are relatively larger than first barbs 174. First barbs 174 are relatively smaller and are located between distal anchor 171 and the plurality of second barbs 176 to provide extra lift in the second direction after insertion.

Figure 11:
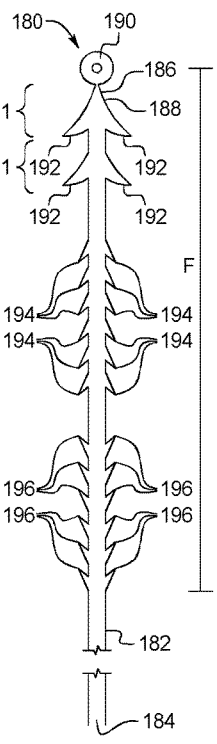
FIG. 11 shows an example embodiment of a suspension implant according to the present disclosure.

FIG. 11 is an alternative example embodiment of a suspension implant 180 according to the present disclosure. In the illustrated embodiment, suspension implant 180 includes an elongated body 182 having a proximal end 184 and a distal end 186, a pointed tip 188 and a needle attachment member such as a distal loop 190 located at the distal end 186, a plurality of first barbs 192, 194, and a plurality of second barbs 194. Suspension implant 180 is similar to suspension implant 160 but the plurality of first barbs 192 are located at two distal anchors 191 near the distal end 186, as compared to one distal anchor for suspension implant 160. The extra distal anchor 191 provides added resistance at the distal end 186 of suspension implant 180, which can be used to accommodate patients with relatively muscular tissue in the soft palate 42 and/or uvula 44.

Figure 12:
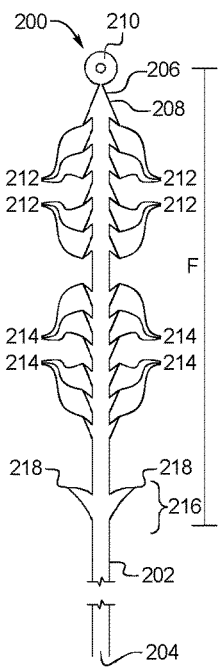
FIG. 12 shows an example embodiment of a suspension implant according to the present disclosure.

FIG. 12 is an alternative example embodiment of a suspension implant 200 according to the present disclosure. In the illustrated embodiment, suspension implant 200 includes an elongated body 202 having a proximal end 204 and a distal end 206, a pointed tip 208 and a needle attachment member such as a distal loop 210 located at the distal end 206, a plurality of first barbs 212, and a plurality of second barbs 214, 218. Suspension implant 200 is similar to suspension implant 100 but includes two different sizes of second barbs 214, 218. Second barbs 218 are located at proximal anchor 216, are closer to proximal end 204, and are relatively larger than second barbs 214. Second barbs 214 are relatively smaller and are located between proximal anchor 216 and the plurality of first barbs 212 to provide extra resistance in the first insertion direction.

Figure 13:
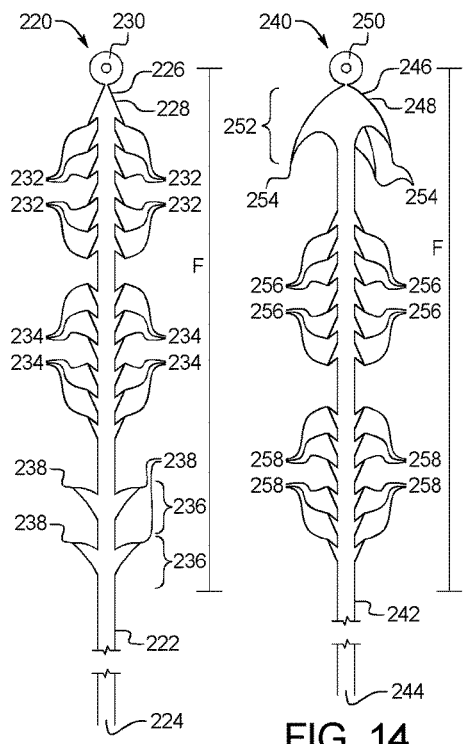
FIG. 13 shows an example embodiment of a suspension implant according to the present disclosure.

FIG. 13 is an alternative example embodiment of a suspension implant 220 according to the present disclosure. In the illustrated embodiment, suspension implant 220 includes an elongated body 222 having a proximal end 224 and a distal end 226, a pointed tip 228 and a needle attachment member such as a distal loop 230 located at the distal end 226, a plurality of first barbs 232, and a plurality of second barbs 234, 238. Suspension implant 220 is similar to suspension implant 200 but the plurality of second barbs 238 are located at two distal anchors 236 near the proximal side of the functional length F of the suspension implant 220, as compared to one distal anchor for suspension implant 200. The extra anchor 236 provides added resistance at the functional length F of the suspension implant 220, which can be used to accommodate patients with relatively muscular tissue in the soft palate 42 and/or uvula 44.

Figure 14:
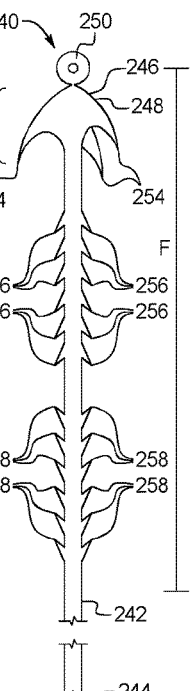
FIG. 14 shows an example embodiment of a suspension implant according to the present disclosure.

FIG. 14 is an alternative example embodiment of a suspension implant 240 according to the present disclosure. In the illustrated embodiment, suspension implant 240 includes an elongated body 242 having a proximal end 244 and a distal end 246, a pointed tip 248 and a needle attachment member such as a distal loop 250 located at the distal end 246, a plurality of first barbs 254, 256, and a plurality of second barbs 258. Suspension implant 240 is similar to suspension implant 140 but includes two different sizes of first barbs 254, 256. First barbs 254 are located at a harpoon-like treble hook anchor 252, are closer to distal end 246, and are relatively larger than first barbs 256. First barbs 256 are relatively smaller and are located between treble hook anchor 252 and the plurality of second barbs 258 to provide extra resistance to the second direction after insertion, for example for a patient with a longer uvula 44. The curvature of first barbs 254 is also more towards the proximal end 244 of suspension implant 240 as opposed to first barbs 256.

Figure 15:
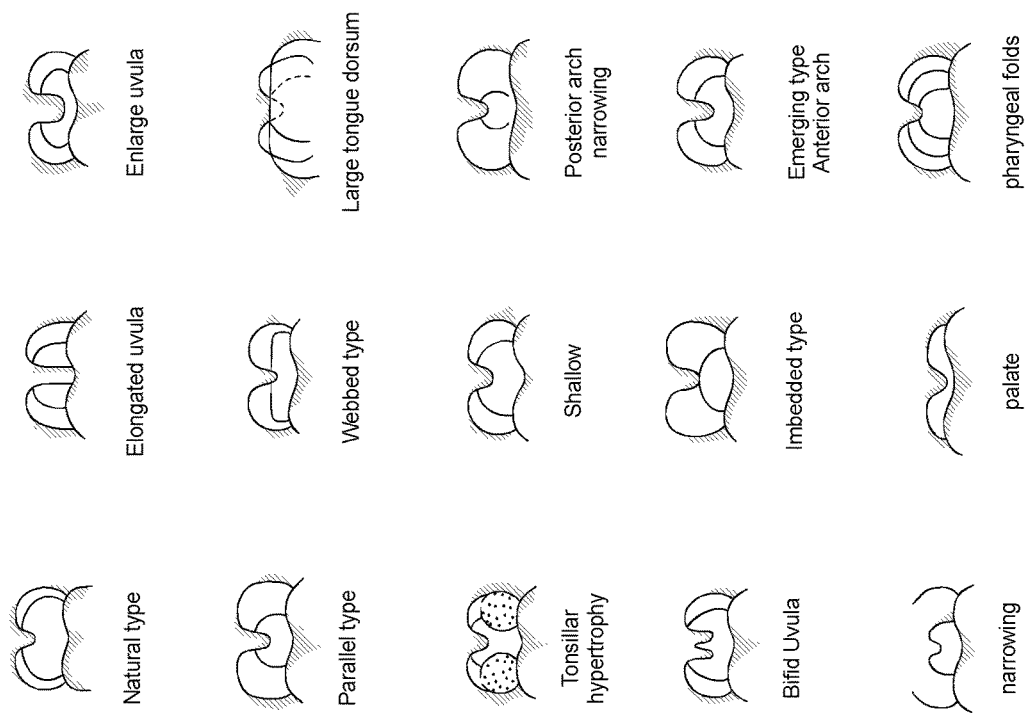
FIG. 15 shows the Ikematsu System for the Diagnosis of Snoring.

Suspension implants 20, 60, 80, 100, 120, 140, 160, 180, 200, 220 and 240 can advantageously be used on different patients with different anatomies. FIG. 15 illustrates the Ikematsu System for the Diagnosis of Snoring. Certain of suspension implants 20, 60, 80, 100, 120, 140, 160, 180, 200, 220 and 240 are better suited for different types of anatomies as shown in FIG. 15. For example, suspension implant 180 is better suited for a patient with an elongated uvula because the extra barbs help hold the increased length of the uvula and the corresponding weight.

Because different suspension implants are better suited for the different anatomies of different patients, it can be advantageous to provide a doctor with an implant kit including two or more of suspension implants 20, 60, 80, 100, 120, 140, 160, 180, 200, 200 and 240. The doctor can then evaluate the patient's uvula and determine which suspension implant is the best fit for the patient.

Figure 19:
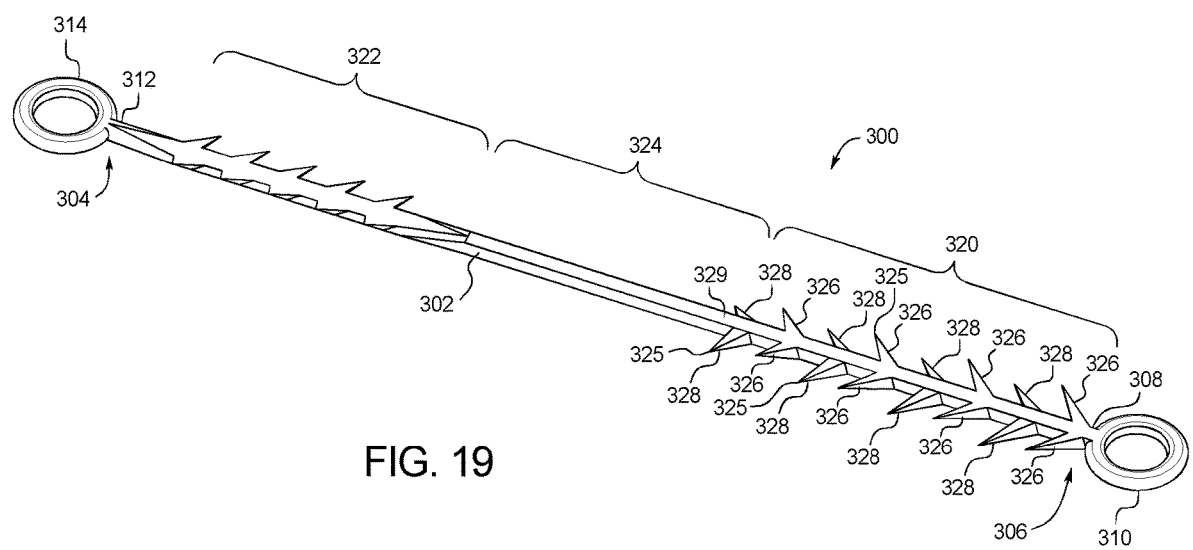
FIG. 19 shows a perspective view of an example embodiment of a suspension implant according to the present disclosure.
Figure 20:
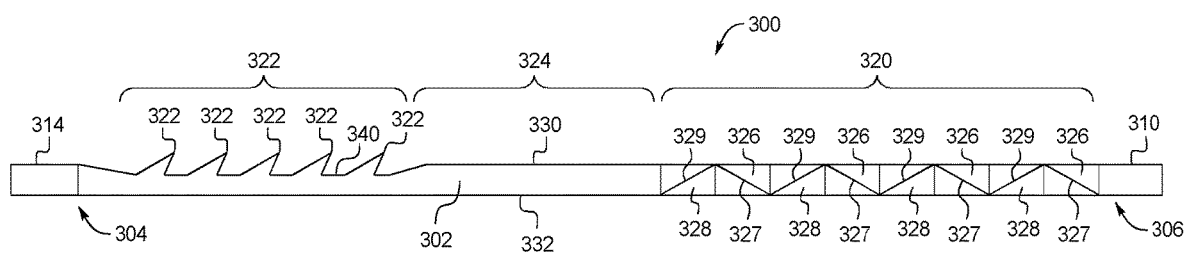
FIG. 20 shows a side view of the suspension implant of FIG. 19.
Figure 21:
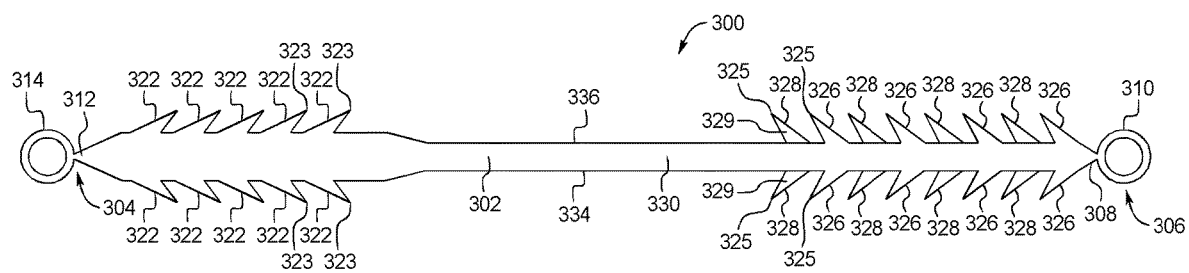
FIG. 21 shows a top view of the suspension implant of FIG. 19.

FIGS. 19 to 21 show an alternative example embodiment of a suspension implant 300 according to the present disclosure. In the illustrated embodiment, suspension implant 300 includes an elongated body 302 having a proximal end 304 and a distal end 306, a pointed tip 308 and a needle attachment member such as a distal loop 310 located at the distal end 306, and a pointed tip 312 and a proximal loop 314 located at the proximal end 304. A plurality of first barbs 320 are located adjacent to distal end 306 and are pointed towards proximal end 304. A plurality of second barbs 322 are located adjacent to proximal end 304 and are pointed towards distal end 306. The plurality of first barbs 320 and the plurality of second barbs 322 are separated by a barbless, smooth portion 324 of the body 302.

In use, suspension implant 300 can be inserted into a patient's soft-palate in a first direction, leading with the distal end 306 of body 302. The proximal end 304 body 300 can then be pulled in a second direction, preferably opposite the first direction, to shorten and stiffen the patient's soft palate. In alternative embodiments, the second direction can be angled with respect to the first insertion direction so as to pull the tissue in a different direction desired by a doctor. Since many patients have differently shaped palates and uvulas, the first and second directions can change from patient to patient.

As proximal end 304 is pulled in the second direction, the plurality of first barbs 320, which are pointed towards the proximal end 304 of suspension implant 300, grab hold of the patient's soft palate 42 and/or uvula 44 to lift and stiffen the muscular tissue in the patient's soft palate 42 and/or uvula 44. The plurality of second barbs 322, which are pointed towards the distal end 306 of suspension implant 300, then hold the patient's soft palate 42 and/or uvula 44 in the lifted and stiffened position when the suspension implant 300 is released from the second direction.

The plurality of first barbs 320 include alternating top barbs 326 and bottom barbs 328. As illustrated in FIGS. 19 to 21, the top barbs 326 extend from opposing side surfaces 334, 336 of body 302 and share the top surface 330 of body 302. The bottom barbs 328 also extend from opposing side surfaces 334, 336 of body 302, but share the bottom surface 332 of body 302. A bottom face 327 of top barbs 326 is angled away from bottom surface 332 towards top surface 330, and a top face 329 of bottom barbs 328 is angled away from top surface 330 towards bottom surface 332. It has been determined that top barbs 326 and bottom barbs 328 are well-suited to provide three-dimensional gripping of the patient's tissue, even with only two rows of barbs protruding from only two side surfaces 334, 336 of body 302, and are easier to mold than a similar implant with barbs extending from each of top surface 330, bottom surface 332, and side surfaces 334, 336.

The plurality of second barbs 322 are located at a recessed surface 340 that is recessed from top surface 330. Recessed surface 340 is designed so that the plurality of second barbs 322 can fold towards each other during insertion of suspension implant 300 into a patient's tissue. In the illustrated embodiment, the width of body 302 increases, and the height of body 302 decreases, at the portion of body 302 that includes the plurality of second barbs 302. The purpose of this configuration is so that the body can flex inwardly when being inserted into the patient's soft tissue, as explained in more detail below. When the body flexes inwardly, the plurality of second barbs 302 can be prevented from resisting the first direction as suspension implant 300 is inserted into the patient's tissue. Then, once suspension implant has been inserted, the plurality of second barbs 302 can be released to grab hold of the patient's tissue. In an embodiment, the plurality of second barbs 322 are flexible to allow for the upward/inward flexing.

Figure 22:
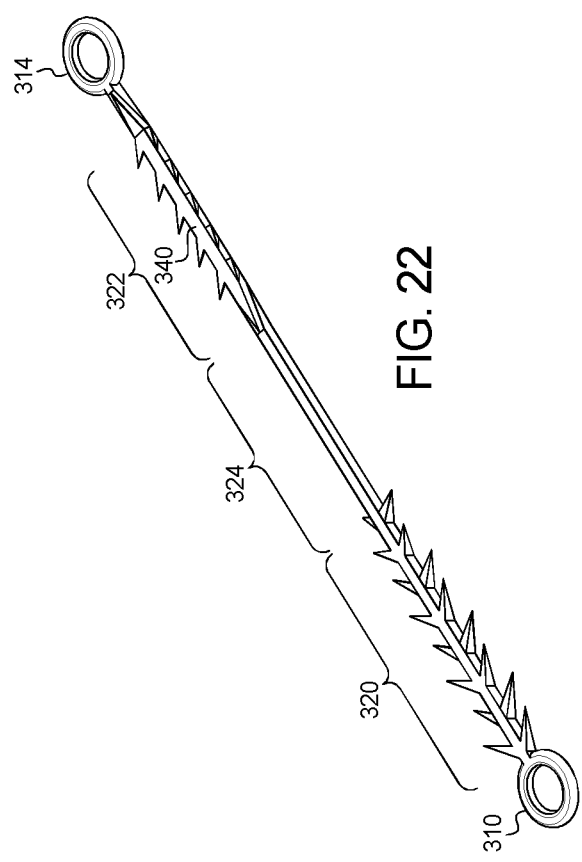
FIG. 22 shows a perspective view of the suspension implant of FIG. 19 in an open configuration.
Figure 23:
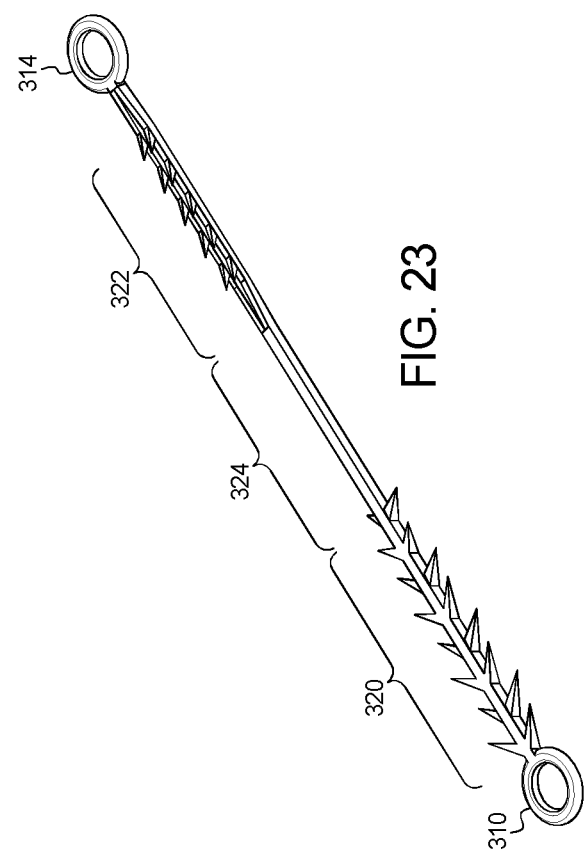
FIG. 23 shows a perspective view of the suspension implant of FIG. 19 in a closed configuration.

FIGS. 22 and 23 show how the plurality of second barbs 322 can fold towards each other for insertion into the patient. In FIG. 22, the plurality of second barbs 322 are shown in an open configuration, in which recessed surface 340 is exposed. In FIG. 23, the plurality of second barbs 322 are shown in a closed configuration, in which the plurality of second barbs 322 on opposing sides have been folded into each other so that the barbs on opposite sides are touching or almost touching. As explained in more detail below, suspension implant 300 can be inserted into the patient with the plurality of second barbs 322 in the closed configuration, and then the plurality of second barbs 322 can be opened once suspension implant 300 has been inserted to grip the patient's tissue.

Proximal loop 314 enables suspension implant 300 to have a smaller design than suspension implants 20, 60, 80, 100, 120, 140, 160, 180, 200, 200 and 240. In an embodiment, the length of suspension implant 300 is about 2.0 to 3.4 cm long, for example 3.4 cm long, compared for example to the length of 30 cm suggested above for suspension implant 20. Proximal loop 314 enables the shorter length of body 302 because an inexpensive thread can be looped through proximal loop 314 during insertion into the patient's tissue. The inexpensive thread can be, for example, an off-the-shelf, non-barbed, throwaway suture 450. The throwaway suture 450 can then be cut and discarded after insertion so that only suspension implant 300 remains in the patient's tissue. Proximal loop 314 therefore also prevents suspension implant 300 from needing to be cut during the insertion process.

In an embodiment, the suspension implant 300 is a flexible, dissolvable material such as a polyester material, for example, a biodegradable thermoplastic aliphatic polyester material such as polyglactic acid, polycaprolactone, polylactic Acid (PLA), or polyglycolic Acid (PGA). Preferably, the material dissolves in a time period sufficient to allow the patient's soft palate and/or uvula to permanently suspend and stiffen, for example, three months. In alternative embodiments, suspension implant 300 can be made of a non-dissolvable material or a material that dissolves in more or less than three months. In another embodiment, suspension implant 300 can include a polycarbonate polyurethane material around body 302 to increase strength.

Figure 24:
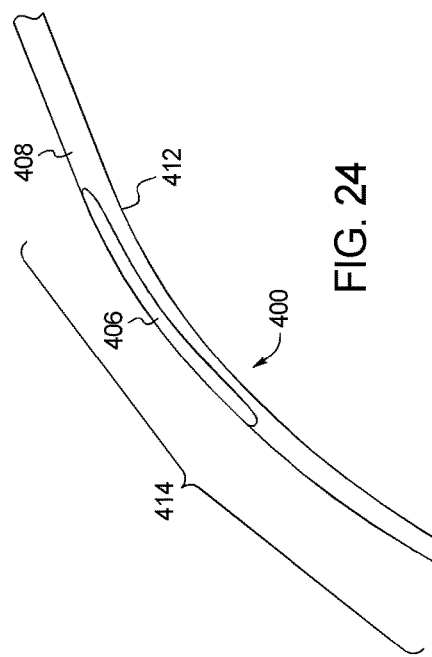
FIG. 24 shows a perspective view of an example embodiment of a needle that can be used to implant a suspension implant according to the present disclosure.

FIG. 24 is an embodiment of a needle 400 that can be used to insert suspension implant 300, or another suspension implant according to the present disclosure, into a patient's soft palate 42 and/or uvula 44. In the illustrated embodiment, needle 400 includes a insertion tip 402, an aperture 404 to receive distal loop 310, and an indentation 406 that is configured to align with the plurality of second barbs 322 of suspension implant 300. The body of needle 400 is advantageously curved for easier insertion into the patient's soft palate, as shown for example in FIG. 18. In an embodiment, the indentation 406 is positioned at the apex of the convex side 408 of the curved portion 414 of needle 400, or in other words at the portion of needle 400 with the smallest radius of curvature. Preferably, indentation 406 is elongated so that it can accept the entirety of the portion of body 302 that includes the plurality of second barbs 322. In an embodiment, the length of indentation 406 along needle 400 is greater than or equal to the length of the plurality of second barbs 322 along body 302 of a corresponding suspension implant 300.

Although the needle attachment member is shown as an open distal loop 310 in FIGS. 19 to 23, it should be understood that the needle attachment member can be an open distal loop with an aperture all the way through, or a closed distal loop similar to a cup-shape loop that can grip a protuberance but does not have an aperture entirely therethough. The needle attachment member can also be a protuberance on the suspension implant 300 that can attach to a slot or corresponding protuberance on the needle.

In the illustrated embodiment, the convex side 408 of the curved portion of needle 400 is the top side shown in FIG. 24, and the concave side 412 of the curved portion of needle 400 is the bottom side shown in FIG. 24. While it is understood that the entire needle could be considered convex because the needle includes a round cross-section, the "convex side" and "concave side" of the needle as referred to herein refer to the opposite top and bottom elongated surfaces along the length of the needle at curved portion 414.

Figure 25:
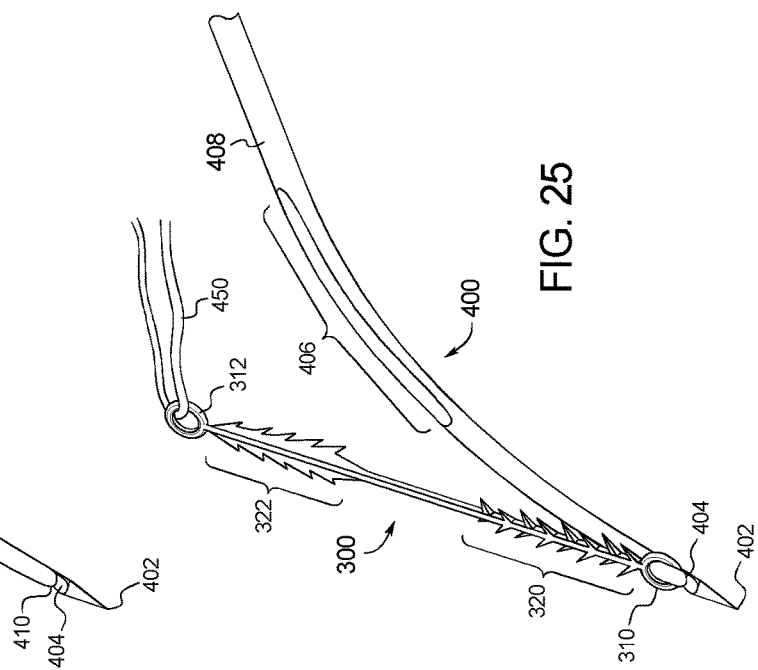
FIG. 25 shows the suspension implant of FIG. 19 being attached to the needle of FIG. 24.
Figure 26:
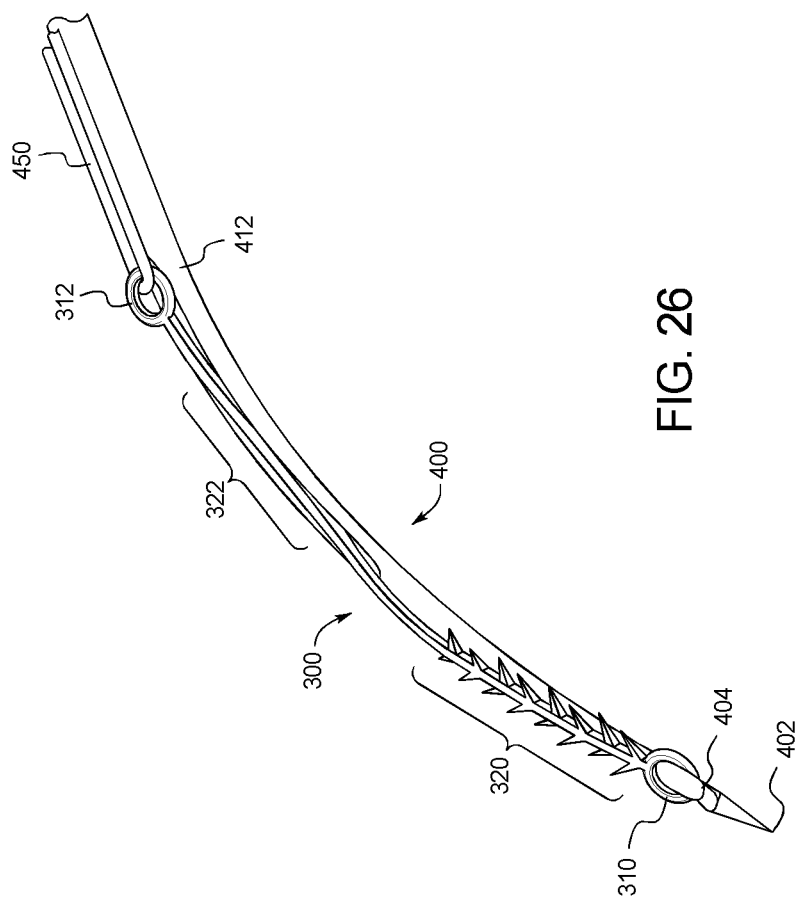
FIG. 26 shows the suspension implant of FIG. 19 being attached to the needle of FIG. 24.

FIGS. 25 and 26 show the attachment of suspension implant 300 to needle 400 so that suspension implant 300 can be inserted into a patient's soft tissue. As illustrated in FIG. 25, distal loop 310 is attached to needle 400 at aperture 404 by looping distal loop 310 over an inner corner 410 of aperture 404. A throwaway, barbless suture 450 is looped through proximal loop 314. The throwaway suture can then be pulled away from insertion tip 402, as illustrated in FIG. 26, so that suspension implant 300 is stretched along the convex side 408 of the body of needle 400 and so that the plurality of second barbs 322 of suspension implant 300 are aligned with and placed into indentation 406 of needle 400.

The placement of the plurality of second barbs 322 within indentation 406 causes the plurality of second barbs 322 to fold towards each other so that the plurality of second barbs 322 do not resist the insertion direction when needle 400 is inserted into the patient's soft palate 42. Even in an embodiment where the plurality of second barbs 322 are not flexible, the side walls of indentation 406 can prevent the plurality of second barbs 322 from resisting the insertion direction when needle 400 is inserted into the patient's soft palate 42.

A separate insertion device can also be used fold the plurality of second barbs 322 and place the plurality of second barbs 322 within indentation 406 of needle 400. In an embodiment, an insertion device can clip onto suspension implant 300 to compress the plurality of second barbs 322 and guide the plurality of second barbs 322 into indentation 406. In another embodiment, an insertion device can clip onto needle 400 and create a funnel shape that guides the plurality of second barbs 322 into indentation 406. In another embodiment, an installation base can lay in a sterile field into which suspension implant 300 is placed. The user can then capture the distal loop 310 of suspension implant 300 with aperture 404 and can use the proximal loop 312 to pull the plurality of second barbs 322 into indentation 406 of needle 400.

Once suspension implant 300 has been attached to needle 400, suspension implant 300 can be inserted into the patient's soft palate 42 by inserting the insertion tip 402 of needle 400 in a first direction into the patient's soft palate 42 so that the insertion tip 402 of the needle 400 extends into the soft palate 42 and optionally also into the base of the uvula 44. Preferably, needle 400 is inserted deep enough into the patient's soft palate 42 and/or uvula 44 so that the entire length of suspension implant 300 is located within the patient's soft palate 42 and/or uvula 44. Sharp tip 308 of suspension implant 300 assists in the insertion of suspension implant 20 into the patient's soft palate 42. Indentation 406 prevents the plurality of second barbs 322 from resisting the insertion direction.

Once the needle 400 and suspension implant 300 have been inserted into the patient's soft palate 42 and/or uvula 44, the needle 400 can be removed from the patient's soft palate 42 and/or uvula 44 in a direction different from the insertion direction. When the needle 400 is being removed from the patient's soft palate 42 in the different direction, the distal loop 310 of suspension implant 300 is released from aperture 404 of needle 400 so that the entire or partial length of the suspension implant 300 remains in the patient's soft palate 42 and/or uvula 44 and only the needle 400 is removed from the tissue. The throwaway suture 450 may also be located partially within the patient's tissue at this stage.

The throwaway suture 450 can then be pulled in a second direction to shorten and stiffen the patient's soft palate 42 and/or uvula 44. In an embodiment, the second direction is substantially opposite to the first insertion direction of the needle 400 and the suspension implant 300 into the patient's soft palate 42. In alternative embodiments, the second direction can be angled with respect to the first insertion direction so as to pull the tissue in a different direction desired by a doctor.

As illustrated, the plurality of first barbs 320 of the suspension implant 300 are located proximal to the distal loop 310. As the throwaway suture 450 of the suspension implant 300 is pulled in the second direction, the pointed tips 325 of each of the plurality of first barbs 320 grab and pull the patient's tissue located near the distal end 306 of body 302, namely, the portion of the patient's soft palate 42 and/or uvula 44 that is obstructing the patient's breathing. The plurality of first barbs 320 are pointed towards the proximal end 304 of suspension implant 300, so the pointed tips 325 of the plurality of first barbs 320 are positioned to dig into the patient's tissue and pull the patient's tissue in the second direction as the plurality of first barbs 320 move in the second direction. This pulling results in the uvula 42 being raised, and the patient's tissue being compressed.

Once the patient's soft palate 42 and/or uvula 44 has been raised by the plurality of first barbs 320, the throwaway suture 450 can be cut or released from proximal loop 314 so that only suspension implant 300 remains in the patient's tissue. Suspension implant 300 will then slightly pull back in the first direction due to the release of the tension from being pulled in the second direction. The plurality of second barbs 322, which are no longer shielded from the patient's tissue by indentation 406, will prevent the patient's soft palate 42 and/or uvula 44 from falling back to its initial position because the plurality of second barbs 322 are pointed towards the distal end 306 of suspension implant 300, so the pointed tips 323 of the plurality of second barbs 322 are positioned to dig into the patient's tissue and resist the initial, first direction. With the plurality of first barbs 320 raising the patient's soft tissue 42 and/or uvula 44 and resisting movement of the patient's soft tissue 42 and/or uvula 44 in the second direction, and the plurality of second barbs 322 resisting movement of the patient's soft tissue 42 and/or uvula 44 in the first direction, the patient's tissue is compressed and remains in a raised position.

In an alternative embodiment, suspension implant 300 can be attached to needle 400 without the need for a throwaway suture 450. For example, needle 400, or a device that includes needle 400, can include a protrusion that is configured to fit through proximal loop 314 and pull proximal loop 314 away from insertion tip 402 so that suspension implant 300 is stretched along the convex side 408 of the body of needle 400 and so that the plurality of second barbs 322 of suspension implant 300 are aligned with and placed into indentation 406 of needle 400. The protrusion can then release suspension implant 300 after needle 400 has been implanted in the patient's tissue.

Figure 27:
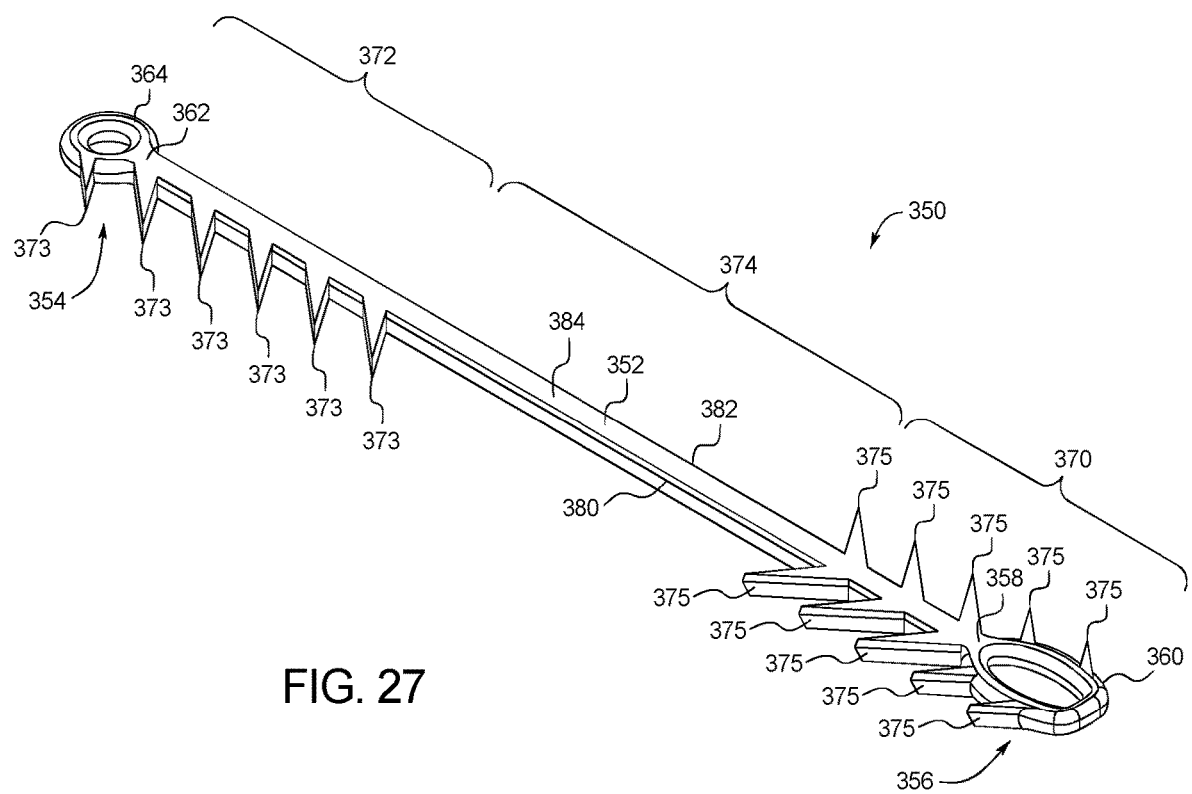
FIG. 27 shows a perspective view of an example embodiment of a suspension implant according to the present disclosure.
Figure 28:
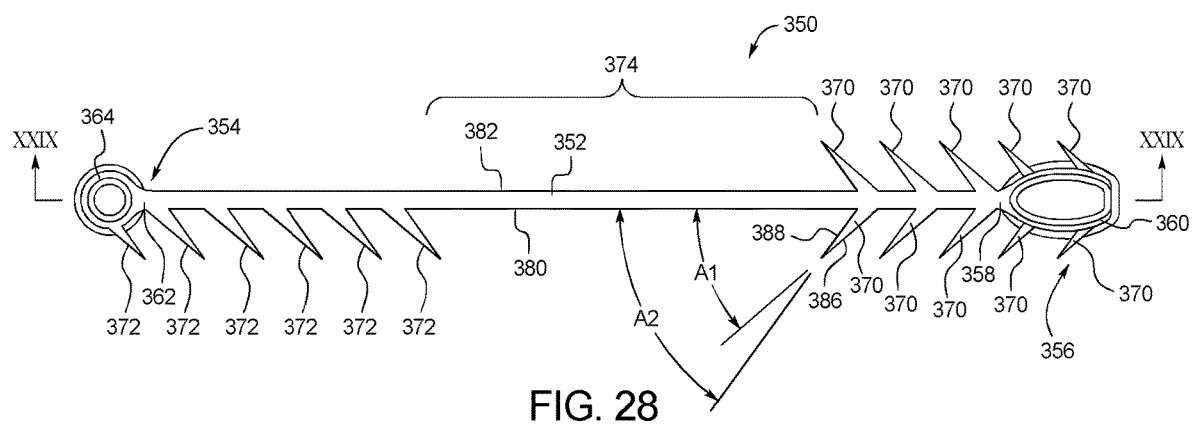
FIG. 28 shows a top view of the suspension implant of FIG. 27.
Figure 29:
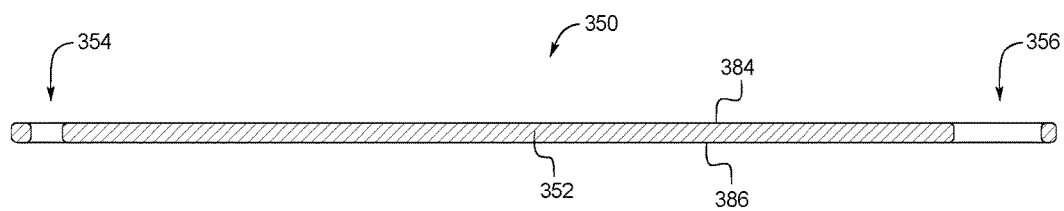
FIG. 29 shows a cross-sectional view of the suspension implant of FIG. 27 taken across lines XXIX-XXIX in FIG. 28.

FIGS. 27 to 29 show an alternative example embodiment of a suspension implant 350 according to the present disclosure. In the illustrated embodiment, suspension implant 350 includes an elongated body 352 having a proximal end 354 and a distal end 356, a pointed tip 358 and a needle attachment member such as a distal loop 360 located at the distal end 356, and a pointed tip 362 and a proximal loop 364 located at the proximal end 354. A plurality of first barbs 370 are located adjacent to distal end 356 and are pointed towards proximal end 354. A plurality of second barbs 372 are located adjacent to proximal end 354 and are pointed towards distal end 356. The plurality of first barbs 370 and the plurality of second barbs 372 are separated by a barbless, smooth portion 374 of body 352.

In use, suspension implant 350 can be inserted into a patient's soft-palate in a first direction, leading with the distal end 356 of body 352. The proximal end 354 body 350 can then be pulled in a second direction, preferably opposite the first direction, to shorten and stiffen the patient's soft palate. In alternative embodiments, the second direction can be angled with respect to the first insertion direction so as to pull the tissue in a different direction desired by a doctor. Since many patients have differently shaped palates and uvulas, the first and second directions can change from patient to patient.

As proximal end 354 is pulled in the second direction, the plurality of first barbs 370, which are pointed towards the proximal end 354 of suspension implant 350, grab hold of the patient's soft palate 42 and/or uvula 44 to lift and stiffen the muscular tissue in the patient's soft palate 42 and/or uvula 44. The plurality of second barbs 372, which are pointed towards the distal end 356 of suspension implant 350, then hold the patient's soft palate 42 and/or uvula 44 in the lifted and stiffened position when the suspension implant 350 is released from the second direction.

In the illustrated embodiment, the plurality of first barbs 370 protrude from both a first side surface 380 and an opposing second side surface 382 of body 352, and share the top surface 384 and/or bottom surface 386 of body 352. The plurality of second barbs 372 only protrude from first side surface 380. As explained in more detail below with reference to FIGS. 30 and 31, the purpose of this configuration with the plurality of second barbs 370 on only one side is so that the plurality of second barbs can be shielded from the patient's tissue as suspension implant 350 is inserted into the patient's tissue, because the plurality of second barbs 372 are pointed opposite of the insertion direction towards the distal end 356 of body 352. In alternative embodiments, the plurality of second barbs 372 can be on second side surface 382, top surface 384 or bottom surface 386.

In the illustrated embodiment, distal loop 360 has a stirrup shape, as compared to the round or oval shape of distal loop 310 of suspension implant 300. That is, the furthest distal portion of distal loop 360 has a flat surface where suspension implant 350 would first enter a patient's tissue. The stirrup shape is advantageous in that it improves the mechanical performance of the disengageable union between the leading end of suspension implant 350 and needle 400 when suspension implant 350 is attached to needle 400. As discussed in more detail below, suspension implant 350 must be pushed or driven into the patient's tissue by needle 400, and the flat surface of the stirrup shape of distal loop 360 complements a flat shape of the inside of indentation 404 of needle 400 and prevents suspension implant 350 from slipping backward during deployment. Although needle 400 can be also be formed with a round or oval shape inside of indentation 404 to compliment the round or oval shape of distal loop 310 of suspension implant 300, it has been determined that the flat surface of the stirrup shape of distal loop 360 engaged to a flat shape of the inside of indentation 404 is more effective at preventing slippage during insertion into the patient's tissue.

Like with suspension implant 300, proximal loop 364 enables suspension implant 350 to have a smaller design than suspension implants 20, 60, 80, 100, 120, 140, 160, 180, 200, 200 and 240. In an embodiment, the length of suspension implant 350 is about 2.0 to 3.4 cm long, for example 2.6 cm long, compared for example to the length of 30 cm suggested above for suspension implant 20. Proximal loop 364 enables the shorter length of body 352 because an inexpensive thread can be looped through proximal loop 364 during insertion into the patient's tissue. The inexpensive thread can be, for example, an off-the-shelf, non-barbed, throwaway suture 450. The throwaway suture 450 can then be cut and discarded after insertion so that only suspension implant 300 remains in the patient's tissue. Proximal loop 364 therefore also prevents suspension implant 350 from needing to be cut during the insertion process.

In an embodiment, the length of suspension implant 350 is about 2.6 cm long, the length of smooth portion 374 is about 1 cm long, and thickness of suspension implant 350 is about 0.05 cm. The plurality of first barbs 370 can extend about 0.18 cm from first side surface 380 and opposing second side surface 382 of body 352, and the plurality of second barbs 372 can extend about 0.18 cm from first side surface 380. The distance between each barb 370, 372 on first side surface 380 and/or second side surface 382 can be about 0.15 cm. A first surface 386 of each of the barbs 370, 372 can be angled at about 40 degrees (angle A1) from first side surface 380 and/or second side surface 382, and a second surface 388 of each of the barbs 370, 372 can be angled at about 55 degrees (angle A2) from first side surface 380 and/or second side surface 382.

In an embodiment, the suspension implant 350 is a flexible, dissolvable material such as a polyester material, for example, a biodegradable thermoplastic aliphatic polyester material such as polyglactic acid, polycaprolactone, polylactic Acid (PLA), or polyglycolic Acid (PGA). Preferably, the material dissolves in a time period sufficient to allow the patient's soft palate and/or uvula to permanently suspend and stiffen, for example, three months. In alternative embodiments, suspension implant 350 can be made of a non-dissolvable material or a material that dissolves in more or less than three months. In another embodiment, suspension implant 350 can include a polycarbonate polyurethane material around body 352 to increase strength.

Figure 30:
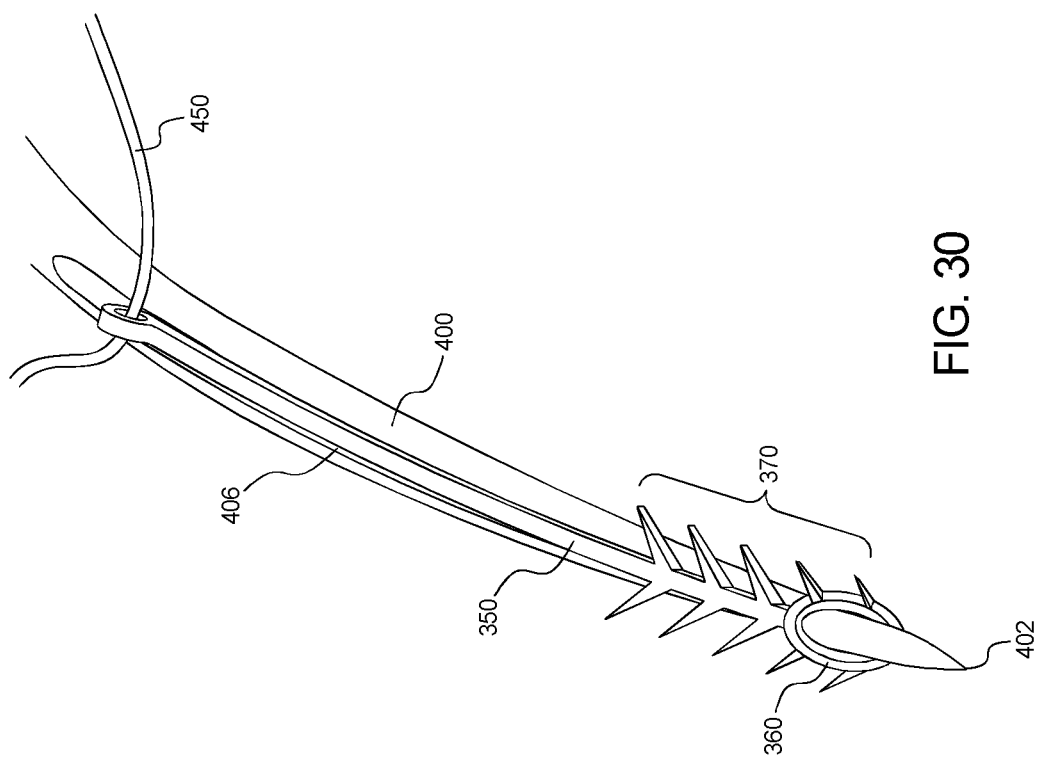
FIG. 30 shows the suspension implant of FIG. 27 being attached to the needle of FIG. 24.
Figure 31:
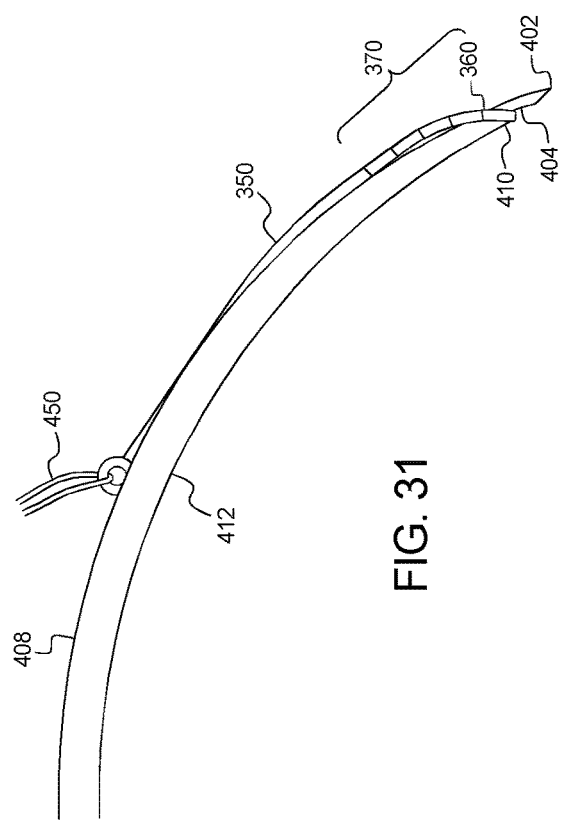
FIG. 31 shows the suspension implant of FIG. 19 being attached to the needle of FIG. 24.

FIGS. 30 and 31 show the attachment of suspension implant 350 to needle 400 so that suspension implant 350 can be inserted into a patient's soft tissue. As illustrated in FIG. 30, distal loop 360 is attached to needle 400 at aperture 404 by looping distal loop 360 over the inner corner 410 of aperture 404, which is shown to be on the concave side 412 of the curved portion of needle 400 in FIGS. 30 and 31. A throwaway, barbless suture 450 is looped through proximal loop 364. The throwaway suture can then be pulled away from insertion tip 402 so that suspension implant 350 is stretched along the convex side 408 of the body of needle 400 and so that the plurality of second barbs 372 of suspension implant 300 are aligned with and placed into indentation 406 of needle 400. As illustrated in FIGS. 30 and 31, suspension implant 350 is twisted while being pulled away from insertion tip 402 so that the plurality of second barbs 372 are placed downward into indentation 406 so that the plurality of second barbs 372 do not resist the insertion direction when needle 400 is inserted into the patient's soft palate 42.

Once suspension implant 350 has been attached to needle 400, suspension implant 350 can be inserted into the patient's soft palate 42 by inserting the insertion tip 402 of needle 400 in a first direction into the patient's soft palate 42 so that the insertion tip 402 of the needle 400 extends into the soft palate 42 and optionally also into the base of the uvula 44. Preferably, needle 400 is inserted deep enough into the patient's soft palate 42 and/or uvula 44 so that the entire length of suspension implant 350 is located within the patient's soft palate 42 and/or uvula 44. Sharp tip 358 of suspension implant 350 assists in the insertion of suspension implant 350 into the patient's soft palate 42. Indentation 406 prevents the plurality of second barbs 372 from resisting the insertion direction.

Once the needle 400 and suspension implant 350 have been inserted into the patient's soft palate 42 and/or uvula 44, the needle 400 can be removed from the patient's soft palate 42 and/or uvula 44 in a direction different from the insertion direction. When the needle 400 is being removed from the patient's soft palate 42 in the different direction, the distal loop 360 of suspension implant 350 is released from aperture 404 of needle 400 so that the entire or partial length of the suspension implant 350 remains in the patient's soft palate 42 and/or uvula 44 and only the needle 400 is removed from the tissue. The throwaway suture 450 may also be located partially within the patient's tissue at this stage.

The throwaway suture 450 can then be pulled in a second direction to shorten and stiffen the patient's soft palate 42 and/or uvula 44. In an embodiment, the second direction is substantially opposite to the first insertion direction of the needle 400 and the suspension implant 350 into the patient's soft palate 42. In alternative embodiments, the second direction can be angled with respect to the first insertion direction so as to pull the tissue in a different direction desired by a doctor.

As illustrated, the plurality of first barbs 370 of the suspension implant 350 are located proximal to the distal loop 360. As the throwaway suture 450 is pulled in the second direction, the pointed tips 375 of each of the plurality of first barbs 370 grab and pull the patient's tissue located near the distal end 356 of body 352, namely, the portion of the patient's soft palate 42 and/or uvula 44 that is obstructing the patient's breathing. The plurality of first barbs 370 are pointed towards the proximal end 354 of suspension implant 350, so the pointed tips 375 of the plurality of first barbs 370 are positioned to dig into the patient's tissue and pull the patient's tissue in the second direction as the plurality of first barbs 370 move in the second direction. This pulling results in the uvula 42 being raised, and the patient's tissue being compressed.

Once the patient's soft palate 42 and/or uvula 44 has been raised by the plurality of first barbs 370, the throwaway suture 450 can be cut or released from proximal loop 364 so that only suspension implant 350 remains in the patient's tissue. Suspension implant 350 will then slightly pull back in the first direction due to the release of the tension from being pulled in the second direction. The plurality of second barbs 372, which are no longer shielded from the patient's tissue by indentation 406, will prevent the patient's soft palate 42 and/or uvula 44 from falling back to its initial position because the plurality of second barbs 372 are pointed towards the distal end 356 of suspension implant 350, so the pointed tips 373 of the plurality of second barbs 372 are positioned to dig into the patient's tissue and resist the initial, first direction. With the plurality of first barbs 370 raising the patient's soft tissue 42 and/or uvula 44 and resisting movement of the patient's soft tissue 42 and/or uvula 44 in the second direction, and the plurality of second barbs 372 resisting movement of the patient's soft tissue 42 and/or uvula 44 in the first direction, the patient's tissue is compressed and remains in a raised position.

In an alternative embodiment, suspension implant 350 can be attached to needle 400 without the need for a throwaway suture 450. For example, needle 400, or a device that includes needle 400, can include a protrusion that is configured to fit through proximal loop 364 and pull proximal loop 364 away from insertion tip 402 so that suspension implant 350 is stretched along the convex side 408 of the body of needle 400 and so that the plurality of second barbs 372 of suspension implant 350 are aligned with and placed into indentation 406 of needle 400. The protrusion can then release suspension implant 350 after needle 400 has been implanted in the patient's tissue.

Figure 32:
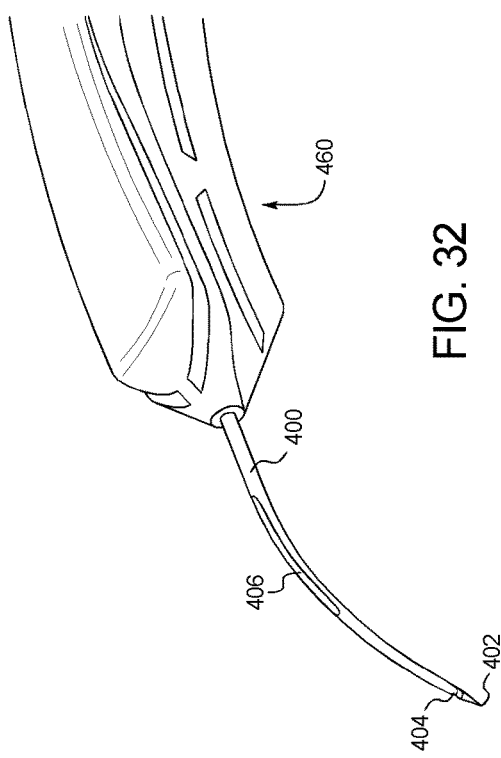
FIG. 32 shows the needle of FIG. 24 as part of an example embodiment of an implant device according to the present disclosure.

FIG. 32 shows an embodiment of a device 460 that can include needle 400 and can be loaded with throwaway suture 450. In an embodiment, device 460 can be configured with a pulling mechanism to pull throwaway suture 450 away from insertion tip 402 to load the plurality of second barbs 322, 374 within indentation 406. Device 460 can also be configured with a cutting mechanism to cut throwaway suture 450 once suspension implant 300, 350 has been inserted into the patient's soft tissue. Device 460 can also be configured with a loop attachment mechanism to grab and hold proximal loop 314, 364 of suspension implant 300, 350 without the need for a throwaway suture 450.

It should be understood that any of the features of the suspension implants 20, 60, 80, 100, 120, 140, 160, 180, 200, 200, 240, 300 and 350 disclosed herein can be used on any of the other suspension implants 20, 60, 80, 100, 120, 140, 160, 180, 200, 200, 240, 300 and 350 disclosed herein.

Modifications in addition to those described above may be made to the structures and techniques described herein without departing from the spirit and scope of the disclosure. Accordingly, although specific embodiments have been described, these are examples only and are not limiting on the scope of the disclosure.

ADDITIONAL ASPECTS OF THE PRESENT DISCLOSURE

Aspects of the subject matter described herein may be useful alone or in combination with any one or more of the other aspect described herein. Without limiting the foregoing description, in a first aspect of the present disclosure, a surgical implant includes a body having a distal end and a proximal end, a needle attachment member located at the distal end of the body, a plurality of first barbs located on the body proximal to the distal end, the plurality of first barbs pointed towards the proximal end of the body, and a plurality of second barbs located on the body between the plurality of first barbs and the proximal end, the plurality of second barbs pointed towards the distal end of the body.

In accordance with a second aspect of the present disclosure, which may be used in combination with any other aspect or combination of aspects listed herein, the needle attachment member includes a distal loop.

In accordance with a third aspect of the present disclosure, which may be used in combination with any other aspect or combination of aspects listed herein, the distal loop includes an aperture therethrough.

In accordance with a fourth aspect of the present disclosure, which may be used in combination with any other aspect or combination of aspects listed herein, the needle attachment member includes a protuberance.

In accordance with a fifth aspect of the present disclosure, which may be used in combination with any other aspect or combination of aspects listed herein, the needle attachment member is located at a tip of the distal end.

In accordance with a sixth aspect of the present disclosure, which may be used in combination with any other aspect or combination of aspects listed herein, the surgical implant includes a pointed tip located at the distal end of the body.

In accordance with a seventh aspect of the present disclosure, which may be used in combination with any other aspect or combination of aspects listed herein, the body is formed of a biodegradable thermoplastic aliphatic polyester.

In accordance with an eighth aspect of the present disclosure, which may be used in combination with any other aspect or combination of aspects listed herein, the body is formed of polyglactic acid, polycaprolactone or any copolymer including polycaprolactone, polylactic Acid (PLA), or polyglycolic Acid (PGA).

In accordance with a ninth aspect of the present disclosure, which may be used in combination with any other aspect or combination of aspects listed herein, the body includes a functional length that is configured to be inserted into the patient's tissue, and the plurality of first barbs and the plurality of second barbs are located within the functional length.

In accordance with a tenth aspect of the present disclosure, which may be used in combination with any other aspect or combination of aspects listed herein, the plurality of first barbs are located at a distal portion of the functional length of the body and the plurality of second barbs are located at a proximal portion of the functional length of the body.

In accordance with an eleventh aspect of the present disclosure, which may be used in combination with any other aspect or combination of aspects listed herein, the functional length includes a first length with only the plurality of first barbs, and a second length with only the plurality of second barbs.

In accordance with a twelfth aspect of the present disclosure, which may be used in combination with any other aspect or combination of aspects listed herein, the first length is located near the distal end of the body, and the second length is located at a proximal portion of functional length.

In accordance with a thirteenth aspect of the present disclosure, which may be used in combination with any other aspect or combination of aspects listed herein, the length along the body of the plurality of first barbs is longer than the length along the body of the plurality of second barbs.

In accordance with a fourteenth aspect of the present disclosure, which may be used in combination with any other aspect or combination of aspects listed herein, the length along the body of the plurality of first barbs is shorter than the length along the body of the plurality of second barbs.

In accordance with a fifteenth aspect of the present disclosure, which may be used in combination with any other aspect or combination of aspects listed herein, the first barbs are larger than the second barbs.

In accordance with a sixteenth aspect of the present disclosure, which may be used in combination with any other aspect or combination of aspects listed herein, the second barbs are larger than the first barbs.

In accordance with a seventeenth aspect of the present disclosure, which may be used in combination with any other aspect or combination of aspects listed herein, at least one of: (i) the plurality of first barbs includes barbs of different sizes; and (ii) the plurality of second barbs includes barbs of different sizes.

In accordance with a eighteenth aspect of the present disclosure, which may be used in combination with any other aspect or combination of aspects listed herein, the surgical implant includes at least one of a distal anchor, a proximal anchor and a treble hook anchor.

In accordance with a nineteenth aspect of the present disclosure, which may be used in combination with any other aspect or combination of aspects listed herein, the curvature of the plurality of first barbs is different than the curvature of the plurality of second barbs.

In accordance with a twentieth aspect of the present disclosure, which may be used in combination with any other aspect or combination of aspects listed herein, the surgical implant lifts and stiffens a patient's tissue.

In accordance with a twenty-first aspect of the present disclosure, which may be used in combination with any other aspect or combination of aspects listed herein, the implant is configured to be inserted into a patient's tissue.

In accordance with a twenty-second aspect of the present disclosure, which may be used in combination with any other aspect or combination of aspects listed herein, the implant is configured to reduce the length of a patient's soft palate.

In accordance with a twenty-third aspect of the present disclosure, which may be used in combination with any other aspect or combination of aspects listed herein, the implant is configured to compress a patient's soft palate.

In accordance with a twenty-fourth aspect of the present disclosure, which may be used in combination with any other aspect or combination of aspects listed herein, a surgical implant includes a body having a distal end, a proximal end and a functional length located proximal to the distal end, the functional length including a first length and a second length, a plurality of first barbs located within the first length proximal to the distal end, the plurality of first barbs pointed towards the proximal end of the body, and a plurality of second barbs located within the second length between the plurality of first barbs and the proximal end, the plurality of second barbs pointed towards the distal end of the body, wherein the first length only includes barbs pointed towards the proximal end of the body and the second length only includes barbs pointed towards the distal end of the body.

In accordance with a twenty-fifth aspect of the present disclosure, which may be used in combination with any other aspect or combination of aspects listed herein, the surgical implant includes a needle attachment member located at the distal end of the body.

In accordance with a twenty-sixth aspect of the present disclosure, which may be used in combination with any other aspect or combination of aspects listed herein, the needle attachment member includes a distal loop.

In accordance with a twenty-seventh aspect of the present disclosure, which may be used in combination with any other aspect or combination of aspects listed herein, the plurality of first barbs includes a distal anchor.

In accordance with a twenty-eighth aspect of the present disclosure, which may be used in combination with any other aspect or combination of aspects listed herein, the plurality of second barbs includes a proximal anchor.

In accordance with a twenty-ninth aspect of the present disclosure, which may be used in combination with any other aspect or combination of aspects listed herein, the plurality of first barbs includes a treble hook anchor.

In accordance with a thirtieth aspect of the present disclosure, which may be used in combination with any other aspect or combination of aspects listed herein, the first length is longer than the second length.

In accordance with a thirty-first aspect of the present disclosure, which may be used in combination with any other aspect or combination of aspects listed herein, the second length is longer than the first length.

In accordance with a thirty-second aspect of the present disclosure, which may be used in combination with any other aspect or combination of aspects listed herein, the implant is configured to reduce the length of a patient's soft palate.

In accordance with a thirty-third aspect of the present disclosure, which may be used in combination with any other aspect or combination of aspects listed herein, the implant is configured to compress a patient's soft palate.

In accordance with a thirty-fourth aspect of the present disclosure, which may be used in combination with any other aspect or combination of aspects listed herein, a surgical implant includes a body having a distal end and a proximal end, a needle attachment member located at the distal end of the body, and a plurality of barbs located on the length of the body proximal to the needle attachment member, wherein the length of the body proximal to the needle attachment member only includes barbs pointed towards the proximal end of the body.

In accordance with a thirty-fifth aspect of the present disclosure, which may be used in combination with any other aspect or combination of aspects listed herein, the surgical implant includes a plurality of second barbs located between the plurality of barbs and the proximal end, wherein the plurality of second barbs are pointed towards the distal end of the body.

In accordance with a thirty-sixth aspect of the present disclosure, which may be used in combination with any other aspect or combination of aspects listed herein, the needle attachment member includes a distal loop.

In accordance with a thirty-seventh aspect of the present disclosure, which may be used in combination with any other aspect or combination of aspects listed herein, the needle attachment member includes a protuberance.

In accordance with a thirty-eighth aspect of the present disclosure, which may be used in combination with any other aspect or combination of aspects listed herein, the needle attachment member is located a tip of the distal end.

In accordance with a thirty-ninth aspect of the present disclosure, which may be used in combination with any other aspect or combination of aspects listed herein, a method of lifting and stiffening a patient's tissue includes attaching a needle attachment member of a suspension implant to a tip of a needle, the needle attachment member located at a distal end of the suspension implant, inserting at least the tip of the needle into the patient's tissue in a first direction while the patient's tissue is in an initial position, removing the needle from the patient's tissue, pulling the suspension implant in a second direction so that a plurality of first barbs of the suspension implant pointed towards a proximal end of the suspension implant pull the patient's tissue in the second direction, and releasing the suspension implant so that a plurality of second barbs of the suspension implant pointed towards the distal end of the suspension implant prevent the patient's tissue from returning to the initial position.

In accordance with a fortieth aspect of the present disclosure, which may be used in combination with any other aspect or combination of aspects listed herein, attaching the needle attachment member of the suspension implant to the tip of the needle includes attaching a distal loop of the suspension implant to the tip of the needle.

In accordance with a forty-first aspect of the present disclosure, which may be used in combination with any other aspect or combination of aspects listed herein, the second direction is opposite the first direction.

In accordance with a forty-second aspect of the present disclosure, which may be used in combination with any other aspect or combination of aspects listed herein, the second direction is angled with respect to the first direction.

In accordance with a forty-third aspect of the present disclosure, which may be used in combination with any other aspect or combination of aspects listed herein, the method includes inserting a functional length of the suspension implant into the patient's soft palate.

In accordance with a forty-fourth aspect of the present disclosure, which may be used in combination with any other aspect or combination of aspects listed herein, the method includes cutting the suspension implant before releasing the suspension implant.

In accordance with a forty-fifth aspect of the present disclosure, which may be used in combination with any other aspect or combination of aspects listed herein, the method includes reducing the length of the patient's soft palate.

In accordance with a forty-sixth aspect of the present disclosure, which may be used in combination with any other aspect or combination of aspects listed herein, the method includes compressing a patient's soft palate.

In accordance with a forty-seventh aspect of the present disclosure, which may be used in combination with any other aspect or combination of aspects listed herein, a kit for lifting and stiffening a patient's tissue includes a container including a first implant including a first body having a first distal end and a first proximal end, a first needle attachment member located at the first distal end, a first plurality of first barbs located on the first body proximal to the first distal end and pointed towards the first proximal end, and a first plurality of second barbs located on the first body between the first plurality of first barbs and the first proximal end and pointed towards the first distal end, and a second implant including a second body having a second distal end and a second proximal end, a second needle attachment member located at the second distal end, a second plurality of first barbs located on the second body proximal to the second distal end and pointed towards the second proximal end, and a second plurality of second barbs located on the second body between the second plurality of first barbs and the second proximal end and pointed towards the second distal end, wherein the first implant and the second implant differ in at least one of: (i) the size of the first plurality of first barbs and the first plurality of second barbs; (ii) the size of the second plurality of first barbs and the second plurality of second barbs; (iii) the length along the first body of the first plurality of first barbs and the length along the second body of the second plurality of first barbs; (iv) the length along the first body of the first plurality of second barbs and the length along the second body of the second plurality of second barbs; (v) the presence or absence of a distal anchor; (vi) the presence or absence of a proximal anchor; (vii) the presence or absence of a treble hook anchor; (viii) the curvature of the first plurality of first barbs and the first plurality of second barbs; and (ix) the curvature of the second plurality of first barbs and the second plurality of second barbs.

In accordance with a forty-eighth aspect of the present disclosure, which may be used in combination with any other aspect or combination of aspects listed herein, the first implant and the second implant differ in the size of the first plurality of first barbs and the first plurality of second barbs.

In accordance with a forty-ninth aspect of the present disclosure, which may be used in combination with any other aspect or combination of aspects listed herein, the first implant and the second implant differ in the size of the second plurality of first barbs and the second plurality of second barbs.

In accordance with a fiftieth aspect of the present disclosure, which may be used in combination with any other aspect or combination of aspects listed herein, the first implant and the second implant differ in the length along the first body of the first plurality of first barbs and the length along the second body of the second plurality of first barbs.

In accordance with a fifty-first aspect of the present disclosure, which may be used in combination with any other aspect or combination of aspects listed herein, the first implant and the second implant differ in the length along the first body of the first plurality of second barbs and the length along the second body of the second plurality of second barbs.

In accordance with a fifty-second aspect of the present disclosure, which may be used in combination with any other aspect or combination of aspects listed herein, the first implant and the second implant differ in the presence or absence of a distal anchor.

In accordance with a fifty-third aspect of the present disclosure, which may be used in combination with any other aspect or combination of aspects listed herein, the first implant and the second implant differ in the presence or absence of a proximal anchor.

In accordance with a fifty-fourth aspect of the present disclosure, which may be used in combination with any other aspect or combination of aspects listed herein, the first implant and the second implant differ in the presence or absence of a treble hook anchor.

In accordance with a fifty-fifth aspect of the present disclosure, which may be used in combination with any other aspect or combination of aspects listed herein, the first implant and the second implant differ in the curvature of the first plurality of first barbs and the first plurality of second barbs.

In accordance with a fifty-sixth aspect of the present disclosure, which may be used in combination with any other aspect or combination of aspects listed herein, the first implant and the second implant differ in the curvature of the second plurality of first barbs and the second plurality of second barbs.

In accordance with a fifty-seventh aspect of the present disclosure, which may be used in combination with any other aspect or combination of aspects listed herein, a surgical implant includes a body having a distal end and a proximal end, the distal end including a needle attachment member configured to be inserted into a patient's soft tissue in a first direction, means for pulling the patient's tissue in a second direction with a plurality of first barbs pointed towards the proximal end, and means for preventing the patient's tissue from returning to an initial position using a plurality of second barbs pointed towards the distal end.

In accordance with a fifty-eighth aspect of the present disclosure, which may be used in combination with any other aspect or combination of aspects listed herein, a surgical implant includes an elongated body having a distal end and a proximal end, a needle attachment member located at the distal end of the body, a proximal loop located at the proximal end of the body, a plurality of first barbs located on the body proximal to the distal end, the plurality of first barbs pointed towards the proximal end of the body, and a plurality of second barbs located on the body proximal to the proximal end, the plurality of second barbs pointed towards the distal end of the body.

In accordance with a fifty-ninth aspect of the present disclosure, which may be used in combination with any other aspect or combination of aspects listed herein, the needle attachment member includes a distal loop.

In accordance with a sixtieth aspect of the present disclosure, which may be used in combination with any other aspect or combination of aspects listed herein, the distal loop includes an aperture therethrough.

In accordance with a sixty-first aspect of the present disclosure, which may be used in combination with any other aspect or combination of aspects listed herein, the needle attachment member includes a protuberance.

In accordance with a sixty-second aspect of the present disclosure, which may be used in combination with any other aspect or combination of aspects listed herein, the needle attachment member is located a tip of the distal end.

In accordance with a sixty-third aspect of the present disclosure, which may be used in combination with any other aspect or combination of aspects listed herein, the surgical implant includes a pointed tip located at the distal end of the body.

In accordance with a sixty-fourth aspect of the present disclosure, which may be used in combination with any other aspect or combination of aspects listed herein, the body is formed of a biodegradable thermoplastic aliphatic polyester.

In accordance with a sixty-fifth aspect of the present disclosure, which may be used in combination with any other aspect or combination of aspects listed herein, the body is formed of polyglactic acid, polycaprolactone or any copolymer including polycaprolactone, polylactic Acid (PLA), or polyglycolic Acid (PGA).

In accordance with a sixty-sixth aspect of the present disclosure, which may be used in combination with any other aspect or combination of aspects listed herein, the plurality of first barbs includes a set of top barbs and a set of bottom barbs.

In accordance with a sixty-seventh aspect of the present disclosure, which may be used in combination with any other aspect or combination of aspects listed herein, the body includes a top surface, a bottom surface and two side surfaces, and wherein the set of top barbs and the set of bottom barbs protrude only from the two side surfaces.

In accordance with a sixty-eighth aspect of the present disclosure, which may be used in combination with any other aspect or combination of aspects listed herein, the top barbs and the bottom barbs alternate along at least one of the two side surfaces.

In accordance with a sixty-ninth aspect of the present disclosure, which may be used in combination with any other aspect or combination of aspects listed herein, the top barbs share the top surface of the body and the bottom barbs share the bottom surface of the body.

In accordance with a seventieth aspect of the present disclosure, which may be used in combination with any other aspect or combination of aspects listed herein, the top barbs extend from the top surface of the body and are flush along the top surface of the body, and the bottom barbs extend from the bottom surface of the body and are flush along the bottom surface of the body.

In accordance with a seventy-first aspect of the present disclosure, which may be used in combination with any other aspect or combination of aspects listed herein, the top barbs include a bottom face that is angled away from the bottom surface, and the bottom barbs include a top face that is angled away from the top surface of the body.

In accordance with a seventy-second aspect of the present disclosure, which may be used in combination with any other aspect or combination of aspects listed herein, a portion of the body that includes the plurality of second barbs has a shorter height than a portion of the body that includes the plurality of first barbs.

In accordance with a seventy-third aspect of the present disclosure, which may be used in combination with any other aspect or combination of aspects listed herein, the plurality of second barbs are flexible so as not to resist insertion into a patient's tissue.

In accordance with a seventy-fourth aspect of the present disclosure, which may be used in combination with any other aspect or combination of aspects listed herein, a portion of the body that includes the plurality of second barbs has a wider width than a portion of the body that includes the plurality of first barbs.

In accordance with a seventy-fifth aspect of the present disclosure, which may be used in combination with any other aspect or combination of aspects listed herein, the body includes a barbless portion between a portion of the body that includes the plurality of second barbs and a portion of the body that includes the plurality of first barbs.

In accordance with a seventy-sixth aspect of the present disclosure, which may be used in combination with any other aspect or combination of aspects listed herein, at least one of: (i) the plurality of first barbs includes only barbs pointed towards the proximal end of the body; and (ii) the plurality of second barbs includes only barbs pointed towards the distal end of the body.

In accordance with a seventy-seventh aspect of the present disclosure, which may be used in combination with any other aspect or combination of aspects listed herein, at least one of: (i) the length along the body of the plurality of first barbs is longer than the length along the body of the plurality of second barbs; (ii) the length along the body of the plurality of first barbs is shorter than the length along the body of the plurality of second barbs; (iii) the first barbs are longer than the second barbs; and (iv) the second barbs are longer than the first barbs.

In accordance with a seventy-eighth aspect of the present disclosure, which may be used in combination with any other aspect or combination of aspects listed herein, at least one of: (i) the plurality of first barbs includes barbs of different sizes; and (ii) the plurality of second barbs includes barbs of different sizes.

In accordance with a seventy-ninth aspect of the present disclosure, which may be used in combination with any other aspect or combination of aspects listed herein, the surgical implant includes at least one of a distal anchor, a proximal anchor and a treble hook anchor.

In accordance with a eightieth aspect of the present disclosure, which may be used in combination with any other aspect or combination of aspects listed herein, the indentation is positioned at an apex of the convex side of the curved body.

In accordance with a eighty-first aspect of the present disclosure, which may be used in combination with any other aspect or combination of aspects listed herein, the plurality of second barbs includes a first plurality of barbs on a first side of the surgical implant, and a second plurality of barbs on a second side of the implant, and wherein the first plurality of barbs and the second plurality of barbs are configured to fold towards each other for insertion into a patient.

In accordance with a eighty-second aspect of the present disclosure, which may be used in combination with any other aspect or combination of aspects listed herein, a portion including the plurality of second barbs decreases in overall width when the first plurality of barbs and the second plurality of barbs fold towards each other.

In accordance with a eighty-third aspect of the present disclosure, which may be used in combination with any other aspect or combination of aspects listed herein, the surgical implant lifts and stiffens a patient's tissue.

In accordance with a eighty-fourth aspect of the present disclosure, which may be used in combination with any other aspect or combination of aspects listed herein, the implant is configured to be inserted into a patient's tissue.

In accordance with a eighty-fifth aspect of the present disclosure, which may be used in combination with any other aspect or combination of aspects listed herein, the body includes a first side surface and an opposite second side surface, and wherein the plurality of second barbs protrude from only the second side surface.

In accordance with a eighty-sixth aspect of the present disclosure, which may be used in combination with any other aspect or combination of aspects listed herein, the implant is configured to reduce the length of a patient's soft palate.

In accordance with a eighty-seventh aspect of the present disclosure, which may be used in combination with any other aspect or combination of aspects listed herein, the implant is configured to compress a patient's soft palate.

In accordance with a eighty-eighth aspect of the present disclosure, which may be used in combination with any other aspect or combination of aspects listed herein, a surgical implant includes an elongated body having a distal end and a proximal end, a needle attachment member located at the distal end of the body, a proximal loop located at the proximal end of the body, and a plurality of barbs located on the body between the distal loop and the proximal loop.

In accordance with a eighty-ninth aspect of the present disclosure, which may be used in combination with any other aspect or combination of aspects listed herein, the needle attachment member includes a distal loop.

In accordance with a ninetieth aspect of the present disclosure, which may be used in combination with any other aspect or combination of aspects listed herein, the needle attachment member includes a protuberance.

In accordance with a ninety-first aspect of the present disclosure, which may be used in combination with any other aspect or combination of aspects listed herein, the plurality of barbs includes: (i) a plurality of first barbs located on the body proximal to the distal end, the plurality of first barbs pointed towards the proximal end of the body; and (ii) a plurality of second barbs located on the body proximal to the proximal end, the plurality of second barbs pointed towards the distal end of the body.

In accordance with a ninety-second aspect of the present disclosure, which may be used in combination with any other aspect or combination of aspects listed herein, at least one of: (i) the plurality of first barbs includes only barbs pointed towards the proximal end of the body; and (ii) the plurality of second barbs includes only barbs pointed towards the distal end of the body.

In accordance with a ninety-third aspect of the present disclosure, which may be used in combination with any other aspect or combination of aspects listed herein, at least one of: (i) the length along the body of the plurality of first barbs is longer than the length along the body of the plurality of second barbs; (ii) the length along the body of the plurality of first barbs is shorter than the length along the body of the plurality of second barbs; (iii) the first barbs are longer than the second barbs; and (iv) the second barbs are longer than the first barbs.

In accordance with a ninety-fourth aspect of the present disclosure, which may be used in combination with any other aspect or combination of aspects listed herein, the body includes a barbless portion between a portion of the body that includes the plurality of second barbs and a portion of the body that includes the plurality of first barbs.

In accordance with a ninety-fifth aspect of the present disclosure, which may be used in combination with any other aspect or combination of aspects listed herein, a device for inserting a surgical implant into a patient's soft tissue includes a curved body including an insertion tip configured to pierce the patient's soft tissue, the curved body having a convex side and an opposing concave side, an elongated indentation located on the convex side of the curved body, and an implant receiving member located between the insertion tip and the elongated indentation on the convex side of the curved body.

In accordance with a ninety-sixth aspect of the present disclosure, which may be used in combination with any other aspect or combination of aspects listed herein, the device includes the surgical implant, the surgical implant including an implant body having a distal loop, wherein the implant receiving member includes an aperture configured to receive the distal loop, and wherein the indentation is configured to receive the implant body.

In accordance with a ninety-seventh aspect of the present disclosure, which may be used in combination with any other aspect or combination of aspects listed herein, the device includes the surgical implant, the surgical implant including an implant body having a protuberance, wherein the implant receiving member includes an aperture configured to receive the protuberance, and wherein the indentation is configured to receive the implant body.

In accordance with a ninety-eighth aspect of the present disclosure, which may be used in combination with any other aspect or combination of aspects listed herein, the device includes the surgical implant, the surgical implant including an implant body having a distal loop, wherein the implant receiving member includes protuberance configured to attach to the distal loop, and wherein the indentation is configured to receive the implant body.

In accordance with a ninety-ninth aspect of the present disclosure, which may be used in combination with any other aspect or combination of aspects listed herein, the surgical implant includes a plurality of barbs protruding from the implant body along a length of the implant body, and wherein the indentation is configured to receive the length of the plurality of barbs.

In accordance with a one-hundredth aspect of the present disclosure, which may be used in combination with any other aspect or combination of aspects listed herein, a length of the indentation along the curved body is longer than the length of the implant body from which the plurality of barbs protrude.

In accordance with a one-hundred-first aspect of the present disclosure, which may be used in combination with any other aspect or combination of aspects listed herein, the indentation is positioned at an apex of the convex side of the curved body.

In accordance with a one-hundred-second aspect of the present disclosure, which may be used in combination with any other aspect or combination of aspects listed herein, the indentation is positioned at a smallest radius of curvature of the curved body.

In accordance with a one-hundred-third aspect of the present disclosure, which may be used in combination with any other aspect or combination of aspects listed herein, the indentation is sunken into the surface of the convex side of the curved body.

In accordance with a one-hundred-fourth aspect of the present disclosure, which may be used in combination with any other aspect or combination of aspects listed herein, a system for lifting and stiffening a patient's tissue includes a surgical implant including an elongated body with a plurality of barbs and a distal end including a needle attachment member, and a device for inserting the surgical implant into the patient's tissue, the device including a curved body having a sharp tip, a receiving member located proximal to the sharp tip and configured to receive the needle attachment member of the surgical implant, and an indentation configured to receive the plurality of barbs.

In accordance with a one-hundred-fifth aspect of the present disclosure, which may be used in combination with any other aspect or combination of aspects listed herein, the needle attachment member includes a distal loop, and the receiving member includes an aperture or a protuberance configured to receive the distal loop.

In accordance with a one-hundred-sixth aspect of the present disclosure, which may be used in combination with any other aspect or combination of aspects listed herein, the needle attachment member includes a protuberance, and the receiving member includes an aperture configured to receive the protuberance or a second protuberance configured to mate with the protuberance.

In accordance with a one-hundred-seventh aspect of the present disclosure, which may be used in combination with any other aspect or combination of aspects listed herein, the system includes at least one thread, and wherein the surgical implant includes a proximal loop located at a proximal end of the elongated body, the proximal loop configured to accept the thread.

In accordance with a one-hundred-eighth aspect of the present disclosure, which may be used in combination with any other aspect or combination of aspects listed herein, the plurality of barbs includes: (i) a plurality of first barbs located on the elongated body proximal to the distal end, the plurality of first barbs pointed towards the proximal end of the elongated body; and (ii) a plurality of second barbs located on the elongated body proximal to the proximal end, the plurality of second barbs pointed towards the distal end of the elongated body.

In accordance with a one-hundred-ninth aspect of the present disclosure, which may be used in combination with any other aspect or combination of aspects listed herein, the surgical implant includes means for preventing the patient's tissue from returning to an initial position using a plurality of second barbs pointed towards the distal end of the body.

In accordance with a one-hundred-tenth aspect of the present disclosure, which may be used in combination with any other aspect or combination of aspects listed herein, the indentation is configured to receive a portion of the elongated body including the plurality of second barbs.

In accordance with a one-hundred-eleventh aspect of the present disclosure, which may be used in combination with any other aspect or combination of aspects listed herein, a length of the indentation along the curved body is longer than the length of the elongated body from which the plurality of barbs protrude.

In accordance with a one-hundred-twelfth aspect of the present disclosure, which may be used in combination with any other aspect or combination of aspects listed herein, the indentation is sunken into a convex side of the curved body of the needle.

In accordance with a one-hundred-thirteenth aspect of the present disclosure, which may be used in combination with any other aspect or combination of aspects listed herein, the indentation is positioned at an apex of the convex side of the curved body of the needle.

In accordance with a one-hundred-fourteenth aspect of the present disclosure, which may be used in combination with any other aspect or combination of aspects listed herein, the indentation is positioned at a smallest radius of curvature of the curved body of the needle.

In accordance with a one-hundred-fifteenth aspect of the present disclosure, which may be used in combination with any other aspect or combination of aspects listed herein, the system includes an insertion device configured to compress the plurality of barbs and guide the plurality of barbs into the indentation.

In accordance with a one-hundred-sixteenth aspect of the present disclosure, which may be used in combination with any other aspect or combination of aspects listed herein, the system includes an insertion device configured to create a funnel shape to guide the plurality of barbs into the indentation.

In accordance with a one-hundred-seventeenth aspect of the present disclosure, which may be used in combination with any other aspect or combination of aspects listed herein, a method of lifting and stiffening a patient's tissue includes attaching a needle attachment member of a suspension implant to a tip of a needle, the needle attachment member located at a distal end of the suspension implant, securing a proximal loop of the suspension implant, the proximal loop located at a proximal end of the suspension implant, inserting at least the tip of the needle into the patient's tissue in a first direction while the patient's tissue is in an initial position, removing the needle from the patient's tissue, pulling the suspension implant in a second direction so that a plurality of first barbs of the suspension implant pointed towards the proximal end of the suspension implant pull the patient's tissue in the second direction, and releasing the proximal loop of the suspension implant so that a plurality of second barbs of the suspension implant pointed towards the distal end of the suspension implant prevent the patient's tissue from returning to the initial position.

In accordance with a one-hundred-eighteenth aspect of the present disclosure, which may be used in combination with any other aspect or combination of aspects listed herein, attaching the needle attachment member of the suspension implant to the tip of the needle includes attaching a distal loop of the suspension implant to the tip of the needle.

In accordance with a one-hundred-nineteenth aspect of the present disclosure, which may be used in combination with any other aspect or combination of aspects listed herein, the second direction is opposite the first direction.

In accordance with a one-hundred-twentieth aspect of the present disclosure, which may be used in combination with any other aspect or combination of aspects listed herein, the second direction is angled with respect to the first direction.

In accordance with a one-hundred-twenty-first aspect of the present disclosure, which may be used in combination with any other aspect or combination of aspects listed herein, securing the proximal loop of the suspension implant includes attaching a thread to the proximal loop.

In accordance with a one-hundred-twenty-second aspect of the present disclosure, which may be used in combination with any other aspect or combination of aspects listed herein, the thread is a barbless suture.

In accordance with a one-hundred-twenty-third aspect of the present disclosure, which may be used in combination with any other aspect or combination of aspects listed herein, pulling the suspension implant in a second direction includes pulling the thread in the second direction.

In accordance with a one-hundred-twenty-fourth aspect of the present disclosure, which may be used in combination with any other aspect or combination of aspects listed herein, releasing the proximal loop of the suspension implant includes cutting the thread.

In accordance with a one-hundred-twenty-fifth aspect of the present disclosure, which may be used in combination with any other aspect or combination of aspects listed herein, securing the proximal loop of the suspension implant includes attaching the proximal loop to the needle.

In accordance with a one-hundred-twenty-sixth aspect of the present disclosure, which may be used in combination with any other aspect or combination of aspects listed herein, attaching the proximal loop to the needle includes attaching the proximal loop to a protrusion of the needle.

In accordance with a one-hundred-twenty-seventh aspect of the present disclosure, which may be used in combination with any other aspect or combination of aspects listed herein, attaching the proximal loop to the needle includes attaching the proximal loop to a device including the needle.

In accordance with a one-hundred-twenty-eighth aspect of the present disclosure, which may be used in combination with any other aspect or combination of aspects listed herein, securing the proximal loop of the suspension implant includes pulling the proximal loop away from the tip of the needle.

In accordance with a one-hundred-twenty-ninth aspect of the present disclosure, which may be used in combination with any other aspect or combination of aspects listed herein, securing the proximal loop of the suspension implant includes securing the proximal loop with a device including the needle.

In accordance with a one-hundred-thirtieth aspect of the present disclosure, which may be used in combination with any other aspect or combination of aspects listed herein, the method includes reducing the length of the patient's soft palate.

In accordance with a one-hundred-thirty-first aspect of the present disclosure, which may be used in combination with any other aspect or combination of aspects listed herein, the method includes compressing a patient's soft palate.

In accordance with a one-hundred-thirty-second aspect of the present disclosure, which may be used in combination with any other aspect or combination of aspects listed herein, a surgical implant includes a body having a distal end and a proximal end, the distal end including a needle attachment member and the proximal end including a proximal loop, means for attaching the needle attachment member proximate to a tip of a needle, and means for pulling the proximal loop away from the tip of the needle to prepare the surgical implant for implantation into a patient's tissue.

In accordance with a one-hundred-thirty-third aspect of the present disclosure, which may be used in combination with any other aspect or combination of aspects listed herein, the surgical implant includes means for lifting the patient's tissue from an initial position with a plurality of first barbs pointed towards the proximal end of the body.

In accordance with a one-hundred-thirty-fourth aspect of the present disclosure, which may be used in combination with any other aspect or combination of aspects listed herein, the surgical implant includes means for preventing the patient's tissue from returning to an initial position using a plurality of second barbs pointed towards the distal end of the body.

In accordance with a one-hundred-thirty-fifth aspect of the present disclosure, which may be used in combination with any other aspect or combination of aspects listed herein, a surgical implant includes a body having a distal end and a proximal end, a needle attachment member located at the distal end of the body, one or more first barbs located on the body proximal to the distal end, the one or more first barbs pointed towards the proximal end of the body, and one or more second barbs located on the body between the one or more first barbs and the proximal end, the one or more second barbs pointed towards the distal end of the body.

In accordance with a one-hundred-thirty-sixth aspect of the present disclosure, which may be used in combination with any other aspect or combination of aspects listed herein, a surgical implant includes an elongated body having a distal end and a proximal end, a needle attachment member located at the distal end of the body, a proximal loop located at the proximal end of the body, one or more first barbs located on the body proximal to the distal end, the one or more first barbs pointed towards the proximal end of the body, and one or more second barbs located on the body proximal to the proximal end, the one or more second barbs pointed towards the distal end of the body.

The invention is claimed as follows:

1. A surgical implant comprising:
   a body extending from a distal end to a proximal end, the body having a first section proximal to the distal end and a second section between the first section and the proximal end;
   a needle attachment member located at the distal end of the body, the needle attachment member including a distal loop, the needle attachment member configured to attach to a needle for insertion of the surgical implant into a patient's tissue;
   a plurality of first barbs located on the first section of the body, the first barbs pointed towards the proximal end of the body; and
   a plurality of second barbs located on the second section of the body, the second barbs pointed towards the distal end of the body, wherein the second barbs are configured to be folded inwardly for insertion of the surgical implant into the patient's tissue by the needle.

2. The surgical implant of claim 1, which is configured to lift and stiffen the patient's tissue when inserted into the patient's tissue.

3. The surgical implant of claim 1, wherein the second section of the body is recessed in comparison to the first section to permit the plurality of second barbs to be folded inwardly.

4. The surgical implant of claim 1, wherein the body includes at least a first side and a second side opposite the first side, the plurality of second barbs protruding from both the first and second sides and configured to fold inwardly towards each other to permit insertion into the patient's tissue.

5. The surgical implant of claim 1, wherein the body includes at least a first side and a second side opposite the first side, the plurality of second barbs protruding from both the first and second sides and configured to fold inwardly so that the second barbs on opposing sides are touching.

6. A system for lifting and stiffening a patient's tissue, the system comprising:
   a surgical implant further comprising
      an implant body extending from a distal end to a proximal end, the implant body having a first section proximal to the distal end and a second section between the first section and the proximal end,
      a distal loop located at the distal end of the implant body,
      a plurality of first barbs located on the first section of the implant body, the first barbs pointed towards the proximal end of the implant body, and
      a plurality of second barbs located on the second section of the implant body, the second barbs pointed towards the distal end of the implant body; and
   an insertion device configured to insert the surgical implant into the patient's tissue, the insertion device further comprising
      a needle extending to a tip,
      a receiving member located proximal to the tip and configured to receive the distal loop of the surgical implant during insertion of the surgical implant into the patient's tissue, and
      an indentation extending along at least a portion of the needle, the indentation configured to align with the plurality of second barbs when the distal loop is received by the receiving member during insertion of the surgical implant into the patient's tissue.

7. The system of claim 6, wherein the receiving member further comprises an aperture configured to receive the distal loop.

8. The system of claim 6, wherein the plurality of second barbs are configured to be folded inwardly when aligned with the indentation.

9. The system of claim 6, wherein the implant body further comprises at least a first side and a second side opposite the first side, the plurality of second barbs protruding from both the first and second sides and configured to fold inwardly towards each other for insertion into the patient's tissue.

10. The system of claim 6, wherein the implant body further comprises at least a first side and a second side opposite the first side, and wherein the second section further comprises the second barbs protruding from the first side of the body and is barbless on the second side of the body.

11. The system of claim 6, wherein the needle includes a curved portion, and wherein the indentation is located on the curved portion.

12. A method of lifting and stiffening a patient's tissue with a surgical implant, the surgical implant including an implant body extending from a distal end to a proximal end, the implant body having a first section proximal to the distal end and a second section between the first section and the proximal end, a distal loop located at the distal end of the implant body, a plurality of first barbs located on the first section of the implant body, the first barbs pointed towards the proximal end of the implant body, and a plurality of second barbs located on the second section of the implant body, the second barbs pointed towards the distal end of the implant body, the method comprising:
 attaching the distal loop proximal to a tip of a needle;
 aligning the second section of the implant body with an indentation in the needle so that the second barbs are pointed inwardly toward the needle;
 inserting at least the tip of the needle into the patient's tissue in a first direction while the patient's tissue is in an initial position;
 removing the needle from the patient's tissue;
 pulling the surgical implant in a second direction so that the plurality of first barbs of the surgical implant pull the patient's tissue in the second direction; and
 releasing the surgical implant so that the plurality of second barbs of the surgical implant prevent the patient's tissue from returning to the initial position.

13. The method of claim 12, wherein aligning the second section includes folding the plurality of second barbs towards each other so that the second barbs are pointed inwardly toward the needle.

14. The method of claim 13, wherein aligning the second section includes twisting the implant body so that the second barbs are pointed inwardly toward the needle.

15. The method of claim 13, wherein aligning the second section includes pulling the proximal end of the implant body away from the distal end.

16. The method of claim 13, which includes securing a thread to a proximal loop located at the proximal end of the implant body when aligning the second section of the implant body with the indentation in the needle.

17. The method of claim 16, wherein releasing the surgical implant includes releasing the thread from the proximal loop of the implant body.

18. The method of claim 16, wherein the thread includes a barbless suture.

19. The method of claim 16, wherein the needle extends from a suture insertion device.

20. A surgical implant comprising:
 a body extending from a distal end to a proximal end, the body having a first section proximal to the distal end and a second section between the first section and the proximal end;
 a needle attachment member located at the distal end of the body, the needle attachment member configured to attach to a needle for insertion of the surgical implant into a patient's tissue;
 a plurality of first barbs located on the first section of the body, the first barbs pointed towards the proximal end of the body; and
 a plurality of second barbs located on the second section of the body, the second barbs pointed towards the distal end of the body, wherein the second barbs are configured to be folded inwardly for insertion of the surgical implant into the patient's tissue by the needle, wherein the second section of the body is recessed in comparison to the first section to permit the plurality of second barbs to be folded inwardly.

* * * * *